(12) United States Patent
Amos et al.

(10) Patent No.: US 10,314,361 B2
(45) Date of Patent: Jun. 11, 2019

(54) FOOTWEAR HAVING SENSOR SYSTEM

(71) Applicant: NIKE, Inc., Beaverton, OR (US)

(72) Inventors: Michael S. Amos, Beaverton, OR (US); James C. Meschter, Portland, OR (US); Matthew A. Nurse, Lake Oswego, OR (US); Andrew A. Owings, Beaverton, OR (US); Jeffrey C. Pisciotta, Oregon City, OR (US); Allan M. Schrock, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 420 days.

(21) Appl. No.: 15/288,472

(22) Filed: Oct. 7, 2016

(65) Prior Publication Data

US 2017/0020224 A1 Jan. 26, 2017

Related U.S. Application Data

(63) Continuation of application No. 12/483,828, filed on Jun. 12, 2009, now Pat. No. 9,462,844.
(Continued)

(51) Int. Cl.
*A43B 3/00* (2006.01)
*A63B 24/00* (2006.01)
(Continued)

(52) U.S. Cl.
CPC .............. *A43B 3/0005* (2013.01); *A43B 3/00* (2013.01); *A43B 17/006* (2013.01); *A43B 17/02* (2013.01); *A61B 5/1038* (2013.01); *A61B 5/486* (2013.01); *A61B 5/6807* (2013.01); *A61B 5/742* (2013.01); *A63B 24/0062* (2013.01); *A63B 69/00* (2013.01); *A63B 69/0028* (2013.01); *G06F 3/0334* (2013.01); *G06F 19/00* (2013.01);
(Continued)

(58) Field of Classification Search
CPC combination set(s) only.
See application file for complete search history.

(56) References Cited

U.S. PATENT DOCUMENTS 3,270,564 A 9/1966 Evans
4,372,558 A 2/1983 Shimamoto et al.
(Continued)

FOREIGN PATENT DOCUMENTS

CA 2668946 A1 5/2008
CN 1839724 A 10/2006
(Continued)

OTHER PUBLICATIONS

Davis, The Re-emergence of the Minimal Running Shoe, Clinical Commentary, Journal of Orthopaedic & Sports Physical Therapy, vol. 44, No. 10, pp. 775-784, Oct. 2014.
(Continued)

*Primary Examiner* — Mohamed Charioui
(74) *Attorney, Agent, or Firm* — Banner & Witcoff, Ltd.

(57) ABSTRACT

A shoe has a sensor system operably connected to a communication port. Performance data is collected by the system and can be transferred for further use via the communication port. The shoe may contain an electronic module configured to gather data from the sensors. The module may also transmit the data to an external device for further processing. Users can use the collected data for a variety of different uses or applications.

22 Claims, 16 Drawing Sheets

Related U.S. Application Data

(60) Provisional application No. 61/138,048, filed on Dec. 16, 2008, provisional application No. 61/061,427, filed on Jun. 13, 2008.

(51) Int. Cl.

| | |
|---|---|
| *A63B 69/00* | (2006.01) |
| *G06F 3/033* | (2013.01) |
| *A43B 17/00* | (2006.01) |
| *A43B 17/02* | (2006.01) |
| *A61B 5/103* | (2006.01) |
| *A61B 5/00* | (2006.01) |
| *G06F 19/00* | (2018.01) |
| *A63B 102/18* | (2015.01) |
| *A63B 26/00* | (2006.01) |
| *A63B 71/06* | (2006.01) |
| *A63B 102/32* | (2015.01) |
| *A63B 102/02* | (2015.01) |
| *A63B 102/22* | (2015.01) |
| *A61B 90/00* | (2016.01) |

(52) U.S. Cl.
CPC . *A61B 2090/064* (2016.02); *A61B 2560/0475* (2013.01); *A63B 26/003* (2013.01); *A63B 2069/0006* (2013.01); *A63B 2071/0638* (2013.01); *A63B 2102/02* (2015.10); *A63B 2102/18* (2015.10); *A63B 2102/182* (2015.10); *A63B 2102/22* (2015.10); *A63B 2102/32* (2015.10); *A63B 2220/12* (2013.01); *A63B 2220/40* (2013.01); *A63B 2220/53* (2013.01); *A63B 2220/836* (2013.01); *A63B 2225/50* (2013.01); *A63B 2243/0025* (2013.01); *A63B 2243/0066* (2013.01); *A63F 2300/1012* (2013.01); *A63F 2300/1031* (2013.01)

(56) References Cited

U.S. PATENT DOCUMENTS

| | | |
|---|---|---|
| 4,373,651 A | 2/1983 | Fanslow |
| 4,518,267 A | 5/1985 | Hepp |
| 4,578,969 A | 4/1986 | Larson |
| 4,647,918 A | 3/1987 | Goforth |
| 4,745,930 A | 5/1988 | Confer |
| 4,814,661 A | 3/1989 | Ratzlaff et al. |
| 4,862,743 A | 9/1989 | Seitz |
| 4,866,412 A | 9/1989 | Rzepczynski |
| 5,010,774 A | 4/1991 | Kikuo et al. |
| 5,033,291 A | 7/1991 | Podoloff et al. |
| 5,047,952 A | 9/1991 | Kramer et al. |
| 5,050,962 A | 9/1991 | Monnier et al. |
| 5,150,536 A | 9/1992 | Strong |
| 5,154,960 A | 10/1992 | Mucci et al. |
| 5,249,967 A | 10/1993 | O'Leary et al. |
| 5,253,656 A | 10/1993 | Rincoe et al. |
| 5,303,131 A | 4/1994 | Wu |
| 5,323,650 A | 6/1994 | Fullen et al. |
| 5,373,651 A | 12/1994 | Wood |
| 5,374,821 A | 12/1994 | Muhs et al. |
| 5,393,651 A | 2/1995 | Hoshi |
| 5,408,873 A | 4/1995 | Schmidt et al. |
| 5,419,562 A | 5/1995 | Cromarty |
| 5,422,521 A | 6/1995 | Neer et al. |
| 5,444,462 A | 8/1995 | Wambach |
| 5,471,405 A | 11/1995 | Marsh |
| 5,500,635 A | 3/1996 | Mott |
| 5,636,146 A | 6/1997 | Flentov et al. |
| 5,636,378 A | 6/1997 | Griffith |
| 5,638,300 A | 6/1997 | Johnson |
| 5,644,858 A | 7/1997 | Bemis |
| 5,655,316 A | 8/1997 | Huang |
| 5,694,514 A | 12/1997 | Evans et al. |
| 5,697,791 A | 12/1997 | Nashner et al. |
| 5,702,323 A | 12/1997 | Poulton |
| 5,714,706 A | 2/1998 | Nakada et al. |
| 5,724,265 A | 3/1998 | Hutchings |
| 5,764,786 A | 6/1998 | Kuwashima et al. |
| 5,785,666 A | 7/1998 | Costello et al. |
| 5,812,142 A | 9/1998 | Small et al. |
| 5,813,142 A | 9/1998 | Demon |
| 5,813,406 A | 9/1998 | Kramer et al. |
| 5,844,861 A | 12/1998 | Maurer |
| 5,889,464 A | 3/1999 | Huang |
| 5,903,454 A | 5/1999 | Hoffberg et al. |
| 5,907,819 A | 5/1999 | Johnson |
| 5,913,727 A | 6/1999 | Ahdoot |
| 5,929,332 A | 7/1999 | Brown |
| 5,960,380 A | 9/1999 | Flentov et al. |
| 5,963,891 A | 10/1999 | Walker et al. |
| 6,017,128 A | 1/2000 | Goldston et al. |
| 6,050,962 A | 4/2000 | Kramer et al. |
| 6,066,075 A | 5/2000 | Poulton |
| 6,081,750 A | 6/2000 | Hoffberg et al. |
| 6,122,340 A | 9/2000 | Darley et al. |
| 6,122,846 A | 9/2000 | Gray et al. |
| 6,148,280 A | 11/2000 | Kramer |
| 6,155,120 A | 12/2000 | Taylor |
| 6,174,294 B1 | 1/2001 | Crabb et al. |
| 6,195,921 B1 | 3/2001 | Truong |
| 6,198,394 B1 | 3/2001 | Jacobsen et al. |
| 6,226,577 B1 | 5/2001 | Yeo |
| 6,266,623 B1 | 7/2001 | Vock et al. |
| 6,287,200 B1 | 9/2001 | Sharma |
| 6,298,314 B1 | 10/2001 | Blackadar et al. |
| 6,330,757 B1 | 12/2001 | Russell |
| 6,336,365 B1 | 1/2002 | Blackadar et al. |
| 6,357,147 B1 | 3/2002 | Darley et al. |
| 6,360,597 B1 | 3/2002 | Hubbard, Jr. |
| 6,426,490 B1 | 7/2002 | Storz |
| 6,428,490 B1 | 8/2002 | Kramer et al. |
| 6,496,787 B1 | 12/2002 | Flentov et al. |
| 6,496,952 B1 | 12/2002 | Osada et al. |
| 6,498,994 B2 | 12/2002 | Vock et al. |
| 6,515,284 B1 | 2/2003 | Valle et al. |
| 6,516,284 B2 | 2/2003 | Flentov et al. |
| 6,536,139 B2 | 3/2003 | Darley et al. |
| 6,539,336 B1 | 3/2003 | Vock et al. |
| 6,544,858 B1 | 4/2003 | Beekman et al. |
| 6,560,903 B1 | 5/2003 | Darley |
| 6,578,291 B2 | 6/2003 | Hirsch et al. |
| 6,611,789 B1 | 8/2003 | Darley |
| 6,640,144 B1 | 10/2003 | Huang et al. |
| 6,656,042 B2 | 12/2003 | Reiss et al. |
| 6,718,200 B2 | 4/2004 | Marmaropoulos et al. |
| 6,739,200 B1 | 5/2004 | Norton |
| 6,748,462 B2 | 6/2004 | Dubil et al. |
| 6,785,579 B2 | 8/2004 | Huang et al. |
| 6,785,805 B1 | 8/2004 | House et al. |
| 6,808,462 B2 | 10/2004 | Snyder et al. |
| 6,829,512 B2 | 12/2004 | Huang et al. |
| 6,836,744 B1 * | 12/2004 | Asphahani ............... A43D 1/02 377/24.2 |
| 6,882,897 B1 | 4/2005 | Fernandez |
| 6,889,282 B2 | 5/2005 | Schollenberger |
| 6,892,216 B2 | 5/2005 | Coburn, II et al. |
| 6,909,420 B1 | 6/2005 | Nicolas et al. |
| 6,922,664 B1 | 7/2005 | Fernandez et al. |
| 6,932,698 B2 | 8/2005 | Sprogis |
| 6,959,259 B2 | 10/2005 | Vock et al. |
| 6,963,818 B2 | 11/2005 | Flentov et al. |
| 6,978,320 B2 | 12/2005 | Nonaka |
| 7,030,861 B1 | 4/2006 | Westerman et al. |
| 7,045,151 B2 | 5/2006 | Trant |
| 7,046,151 B2 | 5/2006 | Dundon |
| 7,054,784 B2 | 5/2006 | Flentov et al. |
| 7,057,551 B1 | 6/2006 | Vogt |
| 7,070,571 B2 | 7/2006 | Kramer et al. |
| 7,092,846 B2 | 8/2006 | Vock et al. |
| 7,152,343 B2 | 12/2006 | Whatley |
| 7,171,331 B2 | 1/2007 | Vock et al. |
| 7,174,277 B2 | 2/2007 | Vock et al. |

(56) References Cited

U.S. PATENT DOCUMENTS

| | | |
|---|---|---|
| 7,200,517 B2 | 4/2007 | Darley et al. |
| 7,245,898 B2 | 7/2007 | Van Bosch et al. |
| 7,277,021 B2 | 10/2007 | Beebe et al. |
| 7,283,647 B2 | 10/2007 | McNitt |
| 7,304,580 B2 | 12/2007 | Sullivan et al. |
| 7,383,728 B2 | 6/2008 | Noble et al. |
| RE40,474 E | 9/2008 | Quellais et al. |
| 7,426,873 B1 | 9/2008 | Kholwadwala et al. |
| 7,428,471 B2 | 9/2008 | Darley et al. |
| 7,433,805 B2 | 10/2008 | Vock et al. |
| 7,457,724 B2 | 11/2008 | Vock et al. |
| 7,497,037 B2 | 3/2009 | Vick et al. |
| 7,498,856 B2 | 3/2009 | Lin et al. |
| 7,498,956 B2 | 3/2009 | Baier et al. |
| 7,513,852 B2 | 4/2009 | Wilkins et al. |
| 7,522,970 B2 | 4/2009 | Fernandez |
| 7,552,549 B2 | 6/2009 | Whittlesey et al. |
| 7,579,946 B2 | 8/2009 | Case, Jr. |
| 7,596,891 B2 | 10/2009 | Carnes et al. |
| 7,607,243 B2 | 10/2009 | Berner, Jr. et al. |
| 7,617,068 B2 | 11/2009 | Tadin et al. |
| 7,620,466 B2 | 11/2009 | Neale et al. |
| 7,623,987 B2 | 11/2009 | Vock et al. |
| 7,625,314 B2 | 12/2009 | Ungari et al. |
| 7,651,442 B2 | 1/2010 | Carlson |
| 7,658,694 B2 | 2/2010 | Ungari |
| 7,670,263 B2 | 3/2010 | Ellis et al. |
| 7,726,206 B2 | 6/2010 | Terrafranca, Jr. et al. |
| 7,739,076 B1 | 6/2010 | Vock et al. |
| 7,758,523 B2 | 7/2010 | Collings et al. |
| 7,771,320 B2 | 8/2010 | Riley et al. |
| 7,805,150 B2 | 9/2010 | Graham et al. |
| 7,816,632 B2 | 10/2010 | Bourke, III et al. |
| 7,840,378 B2 | 11/2010 | Vock et al. |
| 7,901,325 B2 | 3/2011 | Henderson |
| 7,905,815 B2 | 3/2011 | Ellis et al. |
| 7,909,737 B2 | 3/2011 | Ellis et al. |
| 7,921,716 B2 | 4/2011 | Morris Bamberg et al. |
| 7,927,253 B2 | 4/2011 | Vincent et al. |
| 7,934,983 B1 | 5/2011 | Eisner |
| 7,997,007 B2 | 8/2011 | Sanabria-Hernandez |
| 8,056,268 B2 | 11/2011 | DiBenedetto et al. |
| 8,061,061 B1 | 11/2011 | Rivas |
| 8,099,258 B2 | 1/2012 | Alten et al. |
| 8,131,498 B1 | 3/2012 | McCauley |
| 8,142,267 B2 | 3/2012 | Adams |
| 8,172,722 B2 | 5/2012 | Molyneux et al. |
| 8,212,158 B2 | 7/2012 | Wiest |
| 8,216,081 B2 | 7/2012 | Snyder et al. |
| 8,221,290 B2 | 7/2012 | Vincent et al. |
| 8,230,619 B2 | 7/2012 | Salvatelli et al. |
| 8,251,930 B2 | 8/2012 | Ido |
| 8,253,586 B1 | 8/2012 | Matak |
| 8,333,643 B2 | 12/2012 | Eisner |
| 8,467,979 B2 | 6/2013 | Sobolewski |
| 8,474,153 B2 | 7/2013 | Brie et al. |
| 8,479,416 B2 | 7/2013 | Auger et al. |
| 8,484,654 B2 | 7/2013 | Graham et al. |
| 8,676,541 B2 | 3/2014 | Schrock et al. |
| 8,739,639 B2 | 6/2014 | Owings et al. |
| 8,860,584 B1 | 10/2014 | Matak |
| 9,002,680 B2 | 4/2015 | Nurse et al. |
| 9,089,182 B2 | 7/2015 | Schrock et al. |
| 9,445,646 B2 | 9/2016 | Cook et al. |
| 9,462,844 B2 | 10/2016 | Schrock et al. |
| 9,642,415 B2 | 5/2017 | Pease et al. |
| 2001/0003665 A1 | 6/2001 | Kim |
| 2001/0054043 A1 | 12/2001 | Harlan |
| 2002/0035184 A1 | 3/2002 | Plaver et al. |
| 2002/0133069 A1 | 9/2002 | Roberts |
| 2002/0134153 A1 | 9/2002 | Grenlund |
| 2003/0009308 A1 | 1/2003 | Kirtley |
| 2003/0054327 A1 | 3/2003 | Evensen |
| 2003/0097878 A1 | 5/2003 | Farringdon et al. |
| 2003/0163287 A1 | 8/2003 | Vock et al. |
| 2004/0148799 A1 | 8/2004 | Lussier et al. |
| 2004/0154190 A1 | 8/2004 | Munster |
| 2004/0162702 A1 | 8/2004 | Pandipati et al. |
| 2004/0215413 A1 | 10/2004 | Weldum et al. |
| 2004/0218317 A1 | 11/2004 | Kawazu et al. |
| 2004/0225467 A1 | 11/2004 | Vock et al. |
| 2004/0226192 A1 | 11/2004 | Geer et al. |
| 2005/0011085 A1 | 1/2005 | Swigart et al. |
| 2005/0046576 A1 | 3/2005 | Julian et al. |
| 2005/0106977 A1 | 5/2005 | Coulston |
| 2005/0176373 A1 | 8/2005 | Gilbert et al. |
| 2005/0183292 A1 | 8/2005 | DiBenedetto et al. |
| 2005/0184848 A1 | 8/2005 | Yoshida et al. |
| 2005/0188566 A1 | 9/2005 | Whittlesey et al. |
| 2005/0221403 A1 | 10/2005 | Gazenko |
| 2005/0261609 A1 | 11/2005 | Collings et al. |
| 2005/0282633 A1 | 12/2005 | Nicolas et al. |
| 2006/0000420 A1 | 1/2006 | Davies |
| 2006/0010174 A1 | 1/2006 | Nguyen et al. |
| 2006/0017692 A1 | 1/2006 | Wehrenberg et al. |
| 2006/0025282 A1 | 2/2006 | Redmann |
| 2006/0026120 A1 | 2/2006 | Carolan et al. |
| 2006/0053656 A1 | 3/2006 | Kumle |
| 2006/0082977 A1 | 4/2006 | Kim |
| 2006/0091715 A1 | 5/2006 | Schmitz et al. |
| 2006/0143645 A1 | 6/2006 | Vock et al. |
| 2006/0144152 A1 | 7/2006 | Cabuz et al. |
| 2006/0205569 A1 | 9/2006 | Watterson et al. |
| 2006/0248749 A1 | 11/2006 | Ellis |
| 2006/0262120 A1 | 11/2006 | Rosenberg |
| 2006/0270951 A1 | 11/2006 | Ikeuchi |
| 2007/0006489 A1 | 1/2007 | Case et al. |
| 2007/0016091 A1 | 1/2007 | Butt et al. |
| 2007/0021269 A1 | 1/2007 | Shum |
| 2007/0032748 A1 | 2/2007 | McNeil et al. |
| 2007/0033838 A1 | 2/2007 | Luce et al. |
| 2007/0039289 A1 | 2/2007 | LeCompte |
| 2007/0060408 A1 | 3/2007 | Schultz et al. |
| 2007/0063849 A1 | 3/2007 | Rosella et al. |
| 2007/0063850 A1 | 3/2007 | Devaul et al. |
| 2007/0067885 A1 | 3/2007 | Fernandez |
| 2007/0068244 A1 | 3/2007 | Billing et al. |
| 2007/0073178 A1 | 3/2007 | Browning et al. |
| 2007/0078324 A1 | 4/2007 | Wijisiriwardana |
| 2007/0082389 A1 | 4/2007 | Clark et al. |
| 2007/0094890 A1 | 5/2007 | Cho et al. |
| 2007/0118328 A1 | 5/2007 | Vock et al. |
| 2007/0143452 A1 | 6/2007 | Suenbuel et al. |
| 2007/0152812 A1 | 7/2007 | Wong et al. |
| 2007/0156335 A1 | 7/2007 | McBride et al. |
| 2007/0173705 A1 | 7/2007 | Teller et al. |
| 2007/0186446 A1* | 8/2007 | Lafortune ............... A43B 7/142 36/43 |
| 2007/0208544 A1 | 9/2007 | Kulach et al. |
| 2007/0250286 A1 | 10/2007 | Duncan et al. |
| 2007/0260421 A1 | 11/2007 | Berner et al. |
| 2007/0283599 A1 | 12/2007 | Talbott |
| 2008/0009068 A1 | 1/2008 | Georges |
| 2008/0027679 A1 | 1/2008 | Shklarski |
| 2008/0028783 A1 | 2/2008 | Immel et al. |
| 2008/0039203 A1 | 2/2008 | Ackley et al. |
| 2008/0056508 A1 | 3/2008 | Pierce et al. |
| 2008/0060224 A1 | 3/2008 | Whittlesey et al. |
| 2008/0061023 A1 | 3/2008 | Moor |
| 2008/0066343 A1 | 3/2008 | Sanabria-Hernandez |
| 2008/0066560 A1 | 3/2008 | Yu et al. |
| 2008/0127527 A1 | 6/2008 | Chen |
| 2008/0134583 A1 | 6/2008 | Polus |
| 2008/0165140 A1 | 7/2008 | Christie et al. |
| 2008/0172498 A1 | 7/2008 | Boucard |
| 2008/0177507 A1 | 7/2008 | Mian et al. |
| 2008/0188353 A1 | 8/2008 | Vitolo et al. |
| 2008/0203144 A1 | 8/2008 | Kim |
| 2008/0218310 A1 | 9/2008 | Alten et al. |
| 2008/0221403 A1 | 9/2008 | Fernandez |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0259028 A1 | 10/2008 | Teepell et al. |

(56) References Cited

U.S. PATENT DOCUMENTS

| | | |
|---|---|---|
| 2008/0269644 A1 | 10/2008 | Ray |
| 2008/0274755 A1 | 11/2008 | Cholkar et al. |
| 2008/0287832 A1 | 11/2008 | Collins et al. |
| 2008/0289217 A1 | 11/2008 | Horvath |
| 2008/0293023 A1 | 11/2008 | Diehl et al. |
| 2008/0297832 A1 | 12/2008 | Otsuka |
| 2008/0300914 A1 | 12/2008 | Karkanias et al. |
| 2008/0306410 A1 | 12/2008 | Kalpaxis et al. |
| 2008/0307899 A1 | 12/2008 | Von Lilienfeld-Toal et al. |
| 2008/0316325 A1 | 12/2008 | Nakahara |
| 2008/0318679 A1 | 12/2008 | Tran et al. |
| 2009/0018691 A1 | 1/2009 | Fernandez |
| 2009/0027917 A1 | 1/2009 | Chen et al. |
| 2009/0048538 A1 | 2/2009 | Levine et al. |
| 2009/0048918 A1 | 2/2009 | Dawson et al. |
| 2009/0050699 A1 | 2/2009 | Basar et al. |
| 2009/0061837 A1 | 3/2009 | Chaudhri et al. |
| 2009/0075347 A1 | 3/2009 | Cervin et al. |
| 2009/0075781 A1 | 3/2009 | Schwarzberg et al. |
| 2009/0076341 A1 | 3/2009 | James et al. |
| 2009/0105047 A1 | 4/2009 | Guidi et al. |
| 2009/0107009 A1 | 4/2009 | Bishop et al. |
| 2009/0135001 A1 | 5/2009 | Yuk |
| 2009/0137933 A1 | 5/2009 | Lieberman et al. |
| 2009/0149299 A1 | 6/2009 | Tchao et al. |
| 2009/0150178 A1 | 6/2009 | Sutton et al. |
| 2009/0152456 A1 | 6/2009 | Waid et al. |
| 2009/0153369 A1 | 6/2009 | Baier et al. |
| 2009/0153477 A1 | 6/2009 | Saenz |
| 2009/0163287 A1 | 6/2009 | Vald'Via et al. |
| 2009/0167677 A1 | 7/2009 | Kruse et al. |
| 2009/0171614 A1 | 7/2009 | Damen |
| 2009/0233770 A1 | 9/2009 | Vincent et al. |
| 2009/0235739 A1 | 9/2009 | Morris Bamberg et al. |
| 2009/0259566 A1 | 10/2009 | White, III et al. |
| 2009/0262088 A1 | 10/2009 | Moll-Carrillo et al. |
| 2009/0293319 A1 | 12/2009 | Avni |
| 2009/0297832 A1 | 12/2009 | Hatta et al. |
| 2010/0000121 A1 | 1/2010 | Brodie et al. |
| 2010/0004566 A1 | 1/2010 | Son et al. |
| 2010/0009810 A1 | 1/2010 | Trzecieski |
| 2010/0023231 A1 | 1/2010 | Allgaier et al. |
| 2010/0023531 A1 | 1/2010 | Brisebois et al. |
| 2010/0035688 A1 | 2/2010 | Picunko |
| 2010/0053867 A1 | 3/2010 | Ellis et al. |
| 2010/0056340 A1 | 3/2010 | Ellis et al. |
| 2010/0057951 A1 | 3/2010 | Ellis et al. |
| 2010/0059561 A1 | 3/2010 | Ellis et al. |
| 2010/0062740 A1 | 3/2010 | Ellis et al. |
| 2010/0063778 A1 | 3/2010 | Schrock et al. |
| 2010/0063779 A1 | 3/2010 | Schrock et al. |
| 2010/0065836 A1 | 3/2010 | Lee |
| 2010/0082735 A1 | 4/2010 | Petersen et al. |
| 2010/0094147 A1 | 4/2010 | Inan et al. |
| 2010/0111705 A1 | 5/2010 | Sato et al. |
| 2010/0113160 A1 | 5/2010 | Belz et al. |
| 2010/0129780 A1 | 5/2010 | Homsi et al. |
| 2010/0152619 A1 | 6/2010 | Kalpaxis et al. |
| 2010/0152630 A1 | 6/2010 | Matsuoka et al. |
| 2010/0184563 A1 | 7/2010 | Molyneux et al. |
| 2010/0184564 A1 | 7/2010 | Molyneux et al. |
| 2010/0201500 A1 | 8/2010 | Stirling et al. |
| 2010/0225763 A1 | 9/2010 | Vock et al. |
| 2010/0231580 A1 | 9/2010 | Miyasaka |
| 2010/0277617 A1 | 11/2010 | Hollinger |
| 2010/0286601 A1 | 11/2010 | Yodfat et al. |
| 2010/0292599 A1 | 11/2010 | Oleson et al. |
| 2010/0298659 A1 | 11/2010 | McCombie et al. |
| 2010/0312083 A1 | 12/2010 | Southerland |
| 2010/0332188 A1 | 12/2010 | Vock et al. |
| 2011/0003665 A1 | 1/2011 | Burton et al. |
| 2011/0021280 A1 | 1/2011 | Boroda et al. |
| 2011/0087445 A1 | 4/2011 | Sobolewski |
| 2011/0107369 A1 | 5/2011 | O'Brien et al. |
| 2011/0119027 A1 | 5/2011 | Zhu et al. |
| 2011/0119058 A1 | 5/2011 | Berard et al. |
| 2011/0136627 A1 | 6/2011 | Williams |
| 2011/0152695 A1 | 6/2011 | Granqvist et al. |
| 2011/0167678 A1 | 7/2011 | Peikert |
| 2011/0203390 A1 | 8/2011 | Tao et al. |
| 2011/0208444 A1 | 8/2011 | Solinsky |
| 2011/0214501 A1 | 9/2011 | Ross et al. |
| 2012/0035509 A1 | 2/2012 | Wilson et al. |
| 2012/0041767 A1 | 2/2012 | Hoffman et al. |
| 2012/0050351 A1 | 3/2012 | Dobler et al. |
| 2012/0050529 A1 | 3/2012 | Bentley |
| 2012/0059432 A1 | 3/2012 | Emborg et al. |
| 2012/0234111 A1 | 9/2012 | Molyneux et al. |
| 2012/0277040 A1 | 11/2012 | Vincent et al. |
| 2012/0291563 A1 | 11/2012 | Schrock et al. |
| 2012/0291564 A1 | 11/2012 | Amos et al. |
| 2013/0019694 A1 | 1/2013 | Molyneux et al. |
| 2013/0061494 A1 | 3/2013 | Linth |
| 2013/0079907 A1 | 3/2013 | Homsi et al. |
| 2013/0171599 A1 | 7/2013 | Bleich et al. |
| 2013/0190903 A1 | 7/2013 | Balakrishnan et al. |
| 2013/0213145 A1 | 8/2013 | Owings et al. |
| 2013/0213146 A1 | 8/2013 | Amos et al. |
| 2014/0033572 A1 | 2/2014 | Steier et al. |
| 2014/0174205 A1 | 6/2014 | Clarke et al. |
| 2014/0222173 A1 | 8/2014 | Giedwoyn et al. |
| 2014/0259779 A1 | 9/2014 | Hashish et al. |
| 2014/0350435 A1 | 11/2014 | Lam |
| 2015/0257475 A1 | 9/2015 | Langvin et al. |
| 2016/0242500 A1 | 8/2016 | Langvin et al. |
| 2016/0345663 A1 | 12/2016 | Walker et al. |
| 2017/0306539 A1 | 10/2017 | Gladish et al. |

FOREIGN PATENT DOCUMENTS

| | | |
|---|---|---|
| CN | 200994779 Y | 12/2007 |
| CN | 101240461 A | 8/2008 |
| CN | 101367011 A | 2/2009 |
| CN | 101784230 A | 7/2010 |
| CN | 101890215 A | 11/2010 |
| CN | 101894206 A | 11/2010 |
| CN | 102143695 A | 8/2011 |
| CN | 201948063 U | 8/2011 |
| EP | 1707065 A1 | 10/2006 |
| EP | 2189191 A2 | 5/2010 |
| FR | 2929827 A1 | 10/2009 |
| GB | 251054 A | 4/1926 |
| GB | 2421416 A | 6/2006 |
| JP | 56-64301 | 5/1981 |
| JP | S61176429 U | 11/1986 |
| JP | H023020 A | 1/1990 |
| JP | H03-55077 A | 3/1991 |
| JP | H03114209 U | 11/1991 |
| JP | H05161724 A | 6/1993 |
| JP | H06014803 A | 1/1994 |
| JP | H0641505 U | 6/1994 |
| JP | H08-89482 A | 4/1996 |
| JP | H10241648 A | 9/1998 |
| JP | 3036281 B2 | 4/2000 |
| JP | 2000516509 A | 12/2000 |
| JP | 2001351591 A | 12/2001 |
| JP | 2002131155 A | 5/2002 |
| JP | 2002163404 A | 6/2002 |
| JP | 2003061779 A | 3/2003 |
| JP | 2003236002 A | 8/2003 |
| JP | 2004158242 A | 6/2004 |
| JP | 2005019305 A | 1/2005 |
| JP | 2005079019 A | 3/2005 |
| JP | 2005156531 A | 6/2005 |
| JP | 2005270640 A | 10/2005 |
| JP | 2006086072 A | 3/2006 |
| JP | 2006-280955 A | 10/2006 |
| JP | 2007-134473 A | 5/2007 |
| JP | 200715117 | 6/2007 |
| JP | 2008-3752 A | 10/2008 |
| JP | 2009148338 A | 7/2009 |
| JP | 2009535157 A | 10/2009 |
| JP | 2010088886 A | 4/2010 |
| JP | 2011105138 A | 6/2011 |

(56) References Cited

FOREIGN PATENT DOCUMENTS

| | | |
|---|---|---|
| JP | 2011112938 A | 6/2011 |
| JP | 2011524207 A | 9/2011 |
| JP | 2011196931 A | 10/2011 |
| JP | 2012065942 A | 4/2012 |
| JP | 2012115709 A | 6/2012 |
| JP | 2012524638 A | 10/2012 |
| JP | 2013106773 A | 6/2013 |
| JP | 2013537436 A | 10/2013 |
| JP | 2014505577 A | 3/2014 |
| KR | 20010035162 A | 5/2001 |
| KR | 20010079094 A | 8/2001 |
| KR | 20050032119 | 4/2005 |
| KR | 20060021632 | 3/2006 |
| KR | 20060034353 A | 4/2006 |
| KR | 10-2009-0102550 | 9/2009 |
| KR | 20100012845 U | 12/2010 |
| KR | 20100130860 A | 12/2010 |
| KR | 20110071728 A | 6/2011 |
| KR | 20130130051 | 11/2013 |
| KR | 20140004206 A | 1/2014 |
| KR | 20167008215 | 3/2016 |
| WO | 0662600 A1 | 7/1995 |
| WO | 98007341 A2 | 2/1998 |
| WO | 200033031 A1 | 6/2000 |
| WO | 2002035184 A2 | 5/2002 |
| WO | 2006035469 A2 | 4/2006 |
| WO | 2006065679 A2 | 6/2006 |
| WO | 2006067434 A1 | 6/2006 |
| WO | 2006091715 A1 | 8/2006 |
| WO | 2007064735 A2 | 6/2007 |
| WO | 2007082389 A1 | 7/2007 |
| WO | 2007128049 A1 | 11/2007 |
| WO | 2007130287 A2 | 11/2007 |
| WO | 2008061023 A2 | 5/2008 |
| WO | 2008101085 A2 | 8/2008 |
| WO | 2008134583 A1 | 11/2008 |
| WO | 2009027917 A1 | 3/2009 |
| WO | 2009126818 A2 | 10/2009 |
| WO | 2009152456 A2 | 12/2009 |
| WO | 2010065836 A2 | 6/2010 |
| WO | 2010065886 A1 | 6/2010 |
| WO | 2010111705 A2 | 9/2010 |
| WO | 2011157607 A1 | 12/2011 |
| WO | 2012061804 A1 | 5/2012 |
| WO | 2012109244 A1 | 8/2012 |
| WO | 2012112930 A1 | 8/2012 |
| WO | 2012112931 A2 | 8/2012 |
| WO | 2012112934 A2 | 8/2012 |
| WO | 2012112938 A2 | 8/2012 |
| WO | 2012143274 A2 | 10/2012 |

OTHER PUBLICATIONS

Kim, Joo-Tack, STO Ltd., Final Report on IT development cooperative project, "Development of IT running shoes that an transmit athletic information of the shoes when running and development of receiver technology," Ministry of Knowledge Economy (Institute for Information Technology Advancement (ITA)) (Jun. 30, 2009).
Mar. 15, 2017—(EP) ESR—App. No. 16199665.7.
Aug. 7, 2013—(WO) ISR and WO—App. No. PCT/US2013/027397.
Aug. 29, 2013—(WO) International Preliminary Report on Patentability App No. PCT/US2012/025713.
Aug. 24, 2012—(WO) ISR and WO—App. No. PCT/US2012/025717.
Jul. 11, 2012—(WO) ISR & WO App No. PCT/US2012/025709.
Dec. 11, 2009—(WO) ISR and WO App No. PCT/2009/047246.
Morris, Stacy J., A Shoe-Integrated Sensor System for Wireless Gait Analysis and Real-Time Therapeutic Feedback, dissertation, 2004, pp. 1-314, Massachusetts Institute of Technology, MA.
May 28, 2013—(WO) ISR & WO App No. PCT/US2013/027421.
Fleming et al, Athlete and Coach Perceptions of Technology Needs for Evaluating Running Performance, article, Aug. 14, 2010, 18 pages, 13:1-18, UK.
Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.
Mar. 7, 2012—(WO) ISR and WO—App. PCT/US2011/060187.
Jul. 15, 2013—(WO) Search Report and Written Opinion—App. No. PCT/US2013/022219.
Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).
Chee et al, "A low cost wearable wireless sensing system for upper limb home rehabilitation," Robotics Automation and Mechatronics (RAM) 2010 IEEE Conference on Jun. 28-30, 2010; Abstract printout (1 page).
Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).
Jun. 21, 2012—(WO) ISR—App No. PCT/US2012/025701.
Frazier, Karen, "How Many Calories to 1 Carb?" published Nov. 12, 2010, Livestrong.com, 3 pages.
Oct. 1, 2013—(WO) ISR and WO—App No. PCT/US2013/048157.
Llosa et al., "Design of a Motion Detector to Monitor Rowing Performance Based on Wireless Sensor Networks," Intelligent Networking and Collaborativge Systems, 2009, http://ieeexplore.ieee.org/xpl/freeabs_all.jsp?arnumber=5369324 (1 page).
Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/ abstract (1 page).
Morris, "A shoe-integrated sensor system for wireless gait analysis and real-time therapeutic feedback," Harvard-MIT Division of Health Sciences and Technology, 2004,http://dspace.mitedu/handle/1721.1/28601 (3 pages).
Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).
Aylward, "Sensemble : a wireless inertial sensor system for the interactive dance and collective motion analysis," Massachusetts Institute of Technology, School of Architecture and Planning, Program in Media Arts and Sciences, 2006, http://dspace.mitedu/handle/1721.1/37391 (3 pages).
Danko; How to Work a Nike Sensor; Dec. 26, 2010; eHow website; 4 pages.
Coyne; Stout's Shoes on Mass Ave Oldest Shoe Store in the USA; Jun. 18, 2013; FunCityFinder website; 5 pages.
May 8, 2017—(EP) ESR)—App. No. 160201640.

* cited by examiner

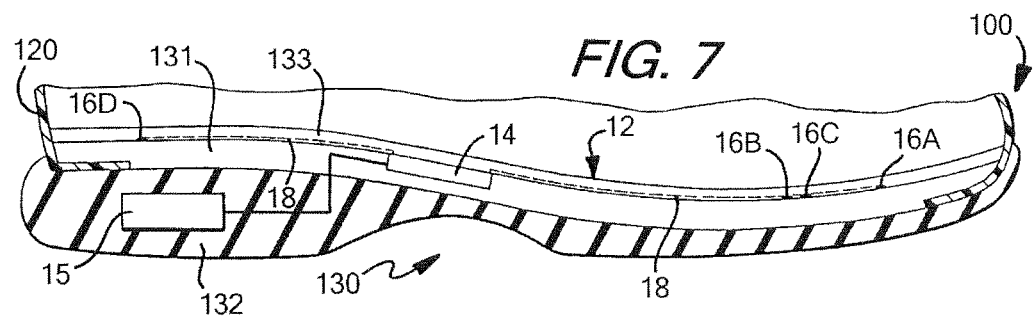
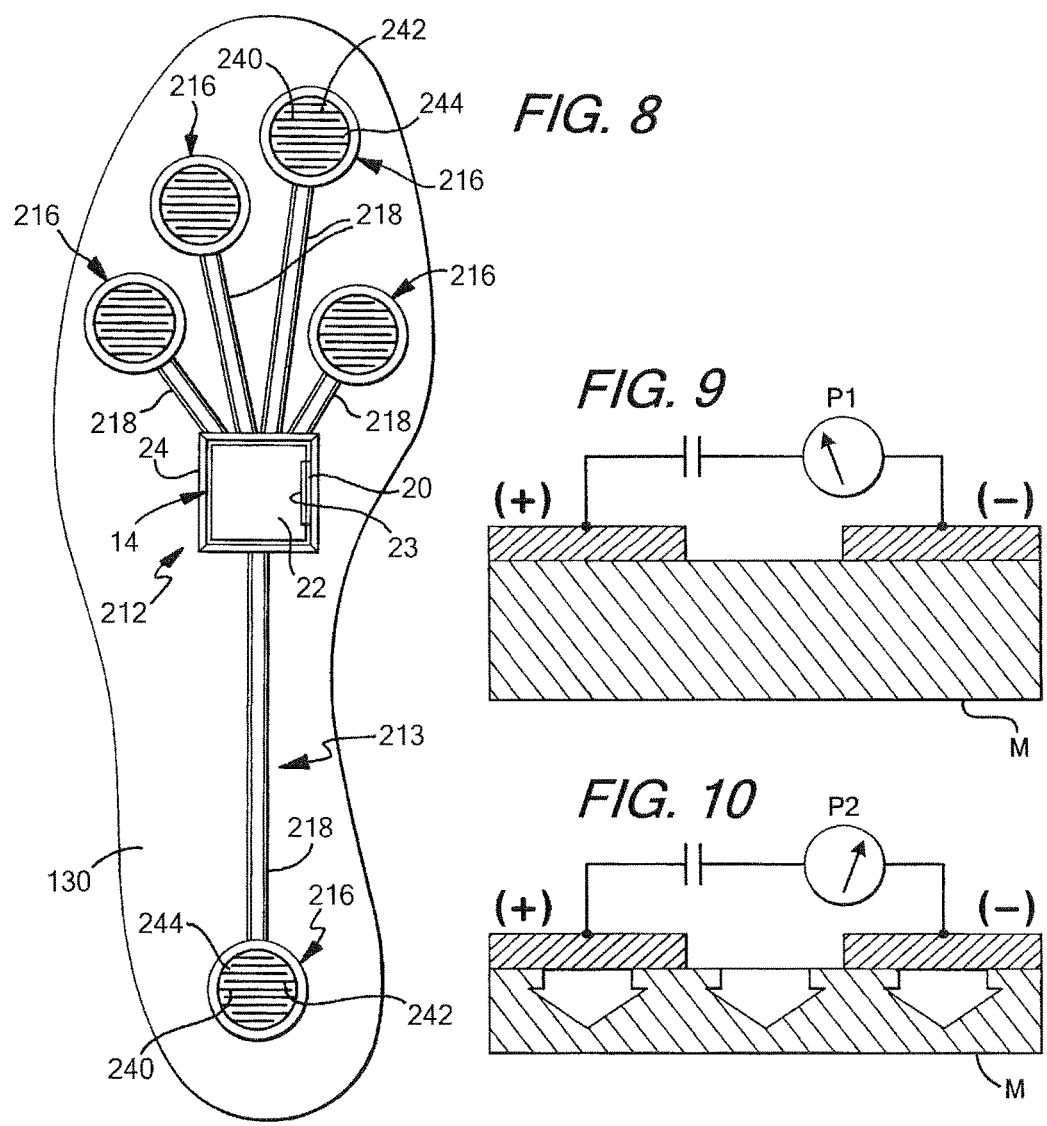

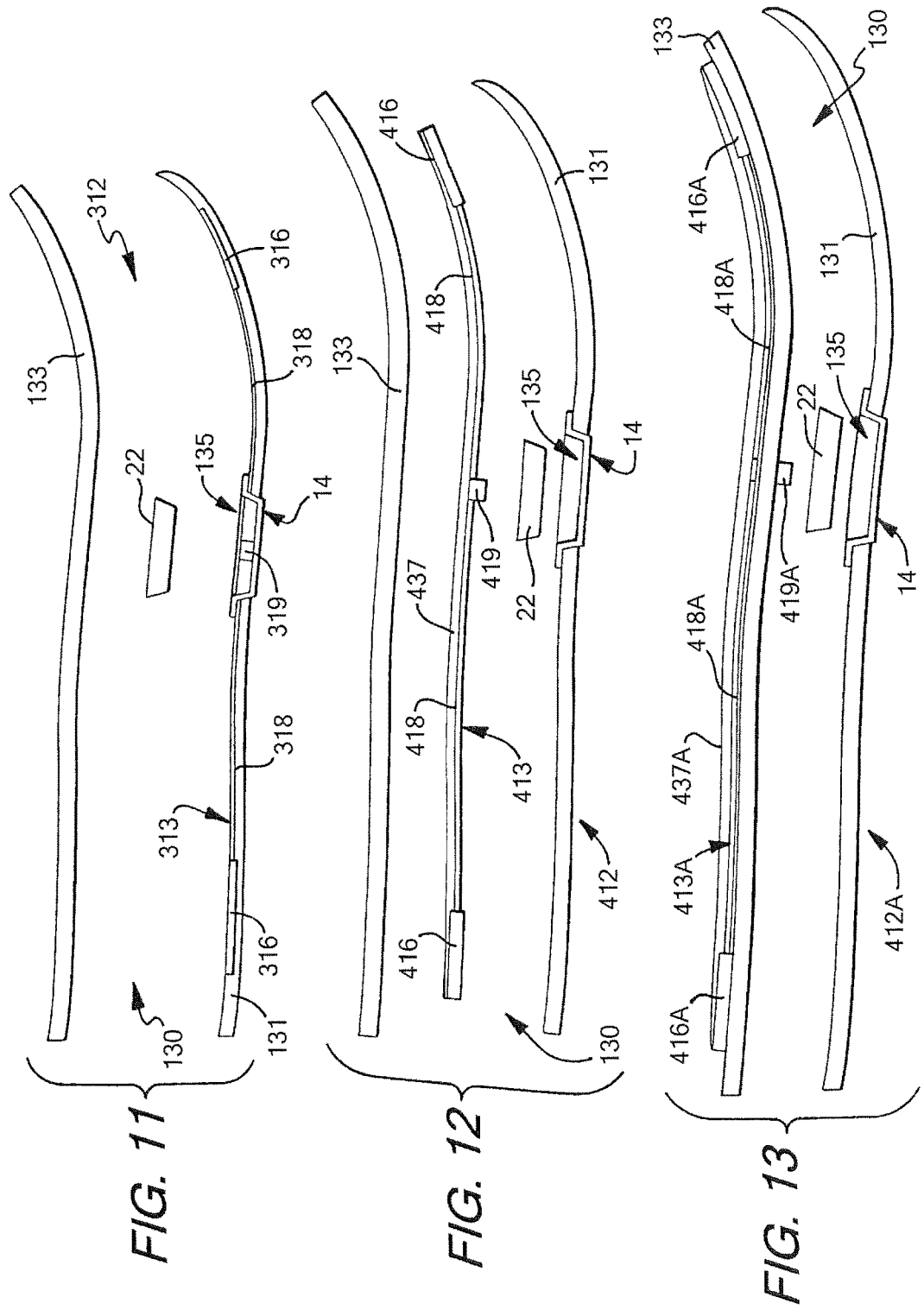

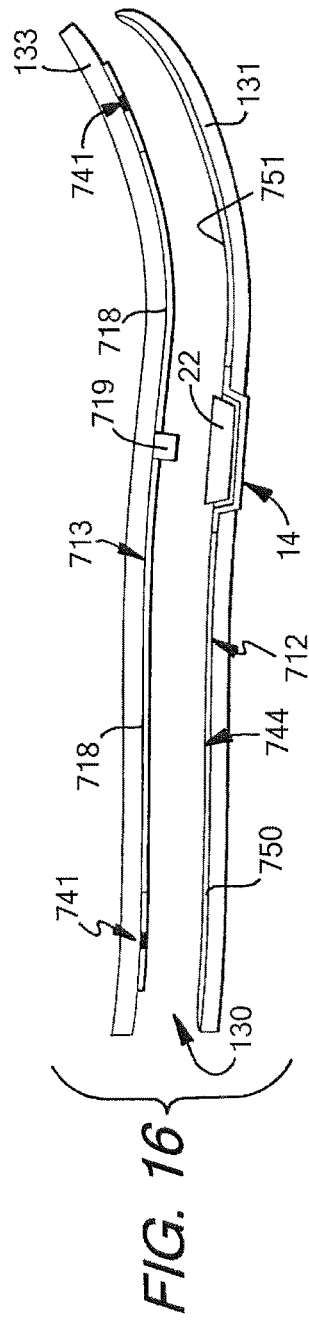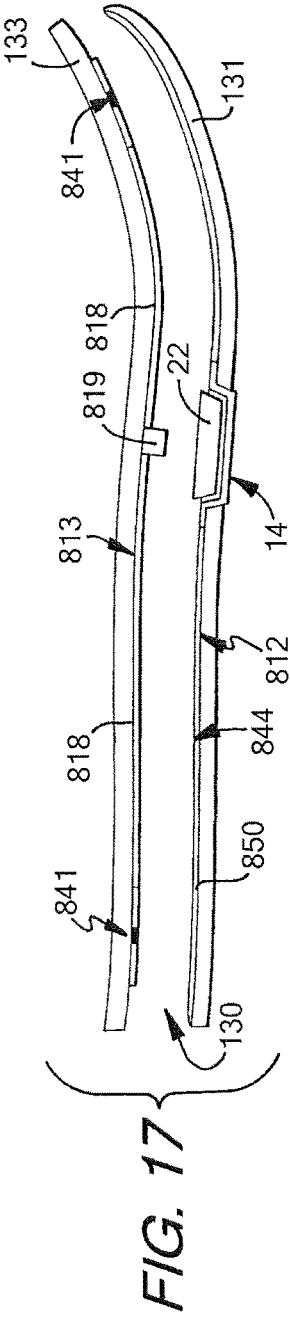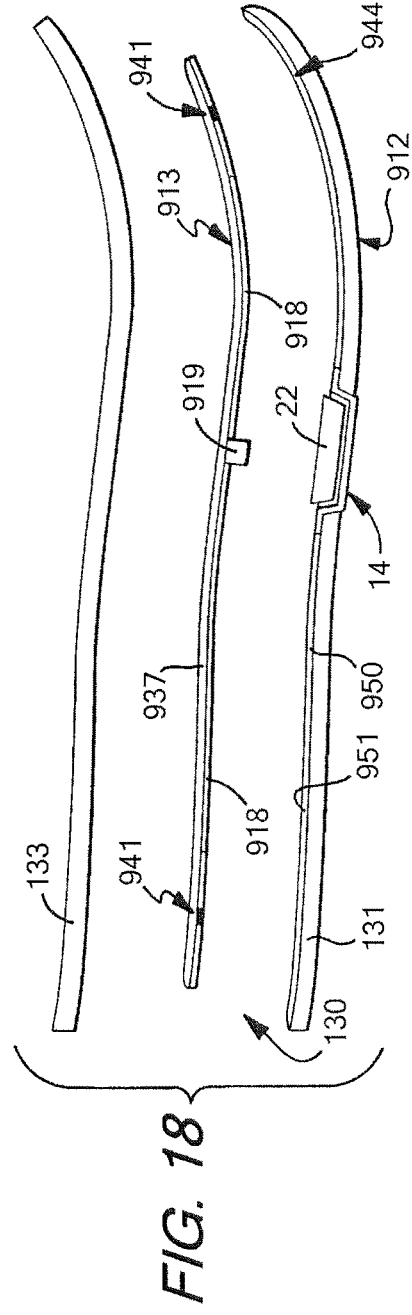

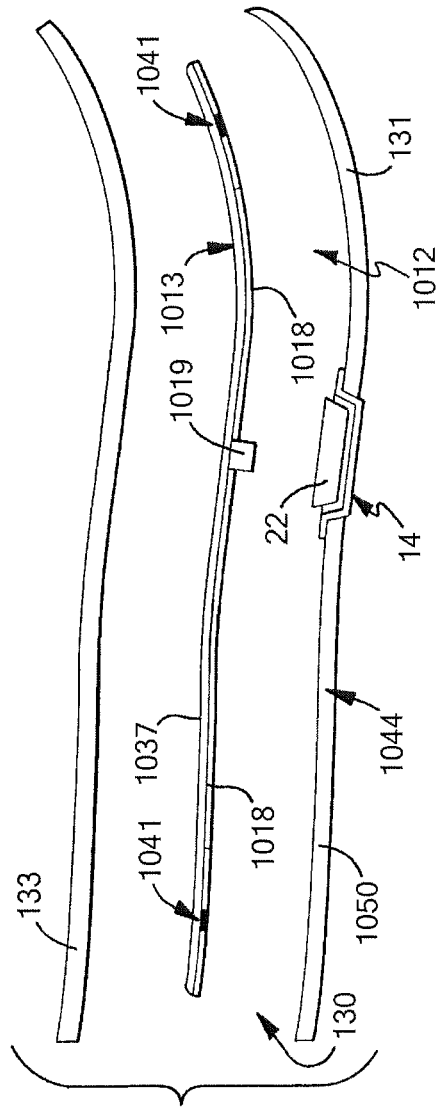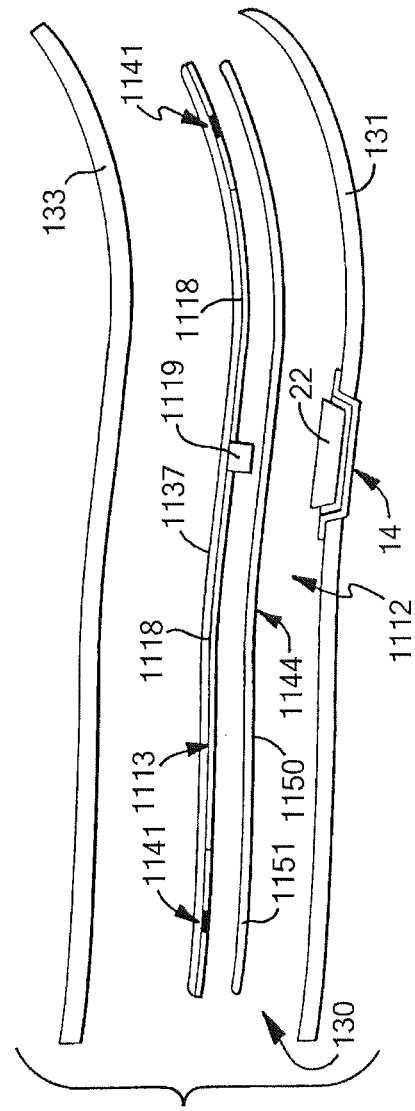

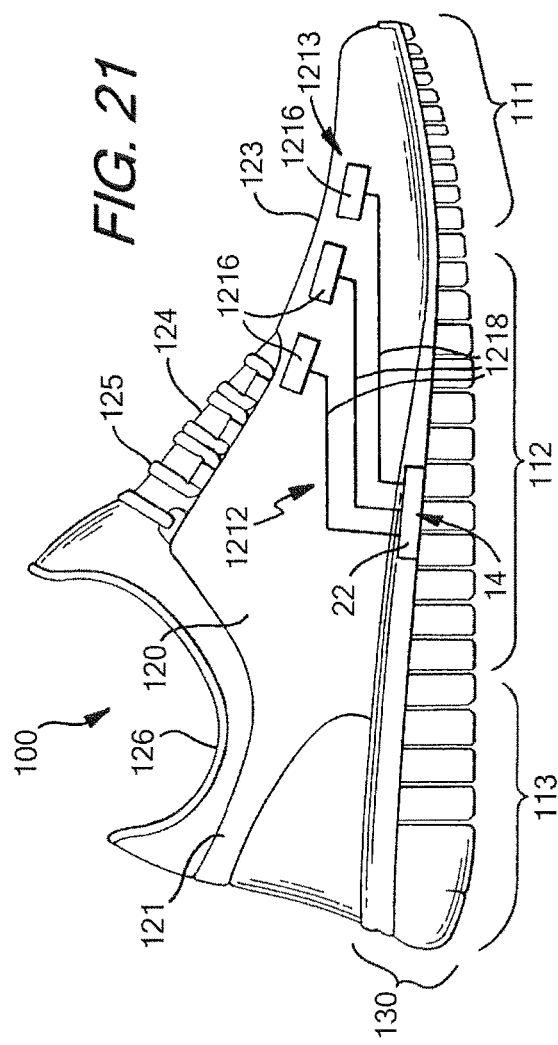
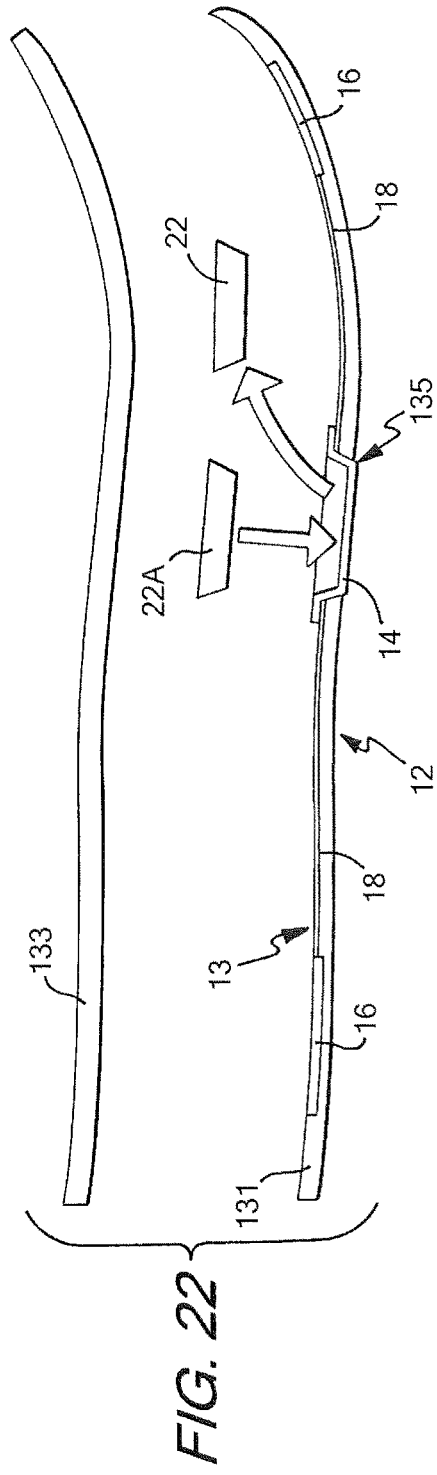

FOOTWEAR HAVING SENSOR SYSTEM

CROSS-REFERENCE TO RELATED APPLICATIONS

The present application is a continuation application of U.S. patent application Ser. No. 12/483,828, filed on Jun. 12, 2009, which is a non-provisional of and claims priority to U.S. Provisional Patent Application No. 61/061,427, filed on Jun. 13, 2008, and U.S. Provisional Patent Application No. 61/138,048, filed on Dec. 16, 2008, all of which are incorporated by reference herein in their entireties.

TECHNICAL FIELD

The present invention generally relates to footwear having a sensor system and, more particularly, to a shoe having a force sensor assembly operably connected to a communication port located in the shoe.

BACKGROUND

Shoes having sensor systems incorporated therein are known. Sensor systems collect performance data wherein the data can be accessed for later use such as for analysis purposes. In certain systems, the sensor systems are complex or data can only be accessed or used with certain operating systems. Thus, uses for the collected data can be unnecessarily limited. Accordingly, while certain shoes having sensor systems provide a number of advantageous features, they nevertheless have certain limitations. The present invention seeks to overcome certain of these limitations and other drawbacks of the prior art, and to provide new features not heretofore available.

BRIEF SUMMARY

The present invention relates generally to footwear having a sensor system. Aspects of the invention relate to an article of footwear that includes an upper member and a sole structure, with a sensor system connected to the sole structure. The sensor system includes a plurality of sensors that are configured for detecting forces exerted by a user's foot on the sensor.

According to one aspect, the footwear further contains a communication port operably connected with the sensors. In one embodiment, the communication port is configured for transmitting data regarding forces detected by each sensor in a universally readable format. The port may also be configured for connection to an electronic module to allow communication between the sensors and the module.

According to another aspect, the footwear contains an electronic module in communication with the sensors, which is configured for collecting data from the sensors. The module may be connected with the sensors through the communication port, and may be positioned within a cavity in the footwear. In one embodiment, the module is further configured for transmitting the data to an external device for further processing.

According to another aspect, the footwear may contain a well located in the sole structure that is configured for removably receiving an electronic module. The well may have a communication port connected with the sensors and configured for communication with the module.

According to another aspect, the sensor system further includes a plurality of sensor leads connecting the sensors to the port and/or the electronic module. The leads may also include one or more power leads for supplying power from the port and/or the module to the sensors.

According to a further aspect, the sensors may be one or more various types of sensors. In one embodiment, the sensors are force-sensitive resistor sensors. In another embodiment, the sensors include two electrodes with a force-sensitive resistive material disposed between the electrodes. The electrodes and the force-sensitive material may be disposed on separate members of the sole structure.

According to yet another aspect, the sensor system includes a first sensor located in the first phalange area of the sole structure, a second sensor located in the first metatarsal head area of the sole structure, a third sensor located in the fifth metatarsal head area of the sole structure, and a fourth sensor located in the heel area of the sole structure.

Additional aspects of the invention relate to a foot contacting member or other sole member of the sole structure that has a sensor system as described above, including a plurality of sensors, connected thereto. The foot contacting member or other sole member may be configured for insertion into an article of footwear. In one embodiment, the sole member may include a plurality of electrodes and sensor leads configured to be connected to a force-sensitive material disposed on another sole member.

Further aspects of the invention relate to a system that includes an article of footwear with a sensor system as described above, with an electronic module connected to the sensor system, and an external device configured for communication with the electronic module. The module is configured to receive data from the sensors and to transmit the data to the external device, and the external device is configured for further processing the data.

According to one aspect, the system also includes an accessory device connected to the external device, configured to enable communication between the electronic module and the external device. The accessory device may also be configured for connection to a second external device to enable communication between the electronic module and the second external device.

According to another aspect, the data communicated to the external device can be used in one or more different applications. Such applications can include using the data as control input for a program executed by the external device, such as a game program, or for athletic performance monitoring, among other applications. Athletic performance monitoring can include monitoring one or more performance metrics such as speed, distance, lateral movement, acceleration, jump height, weight transfer, foot strike pattern, balance, foot pronation or supination, loft time measurement during running, lateral cutting force, contact time, center of pressure, weight distribution, and/or impact force, among others.

Still further aspects of the invention relate to methods utilizing an article of footwear containing a sensor system as described above. Such methods can include receiving data from the sensors at the electronic module and transmitting the data from the module to a remote external device for further processing, which may include use in one or more applications. Such methods can also include removing or disconnecting a first electronic module from the sensor system and connecting a second module in its place, where the second module is configured for a different operation. Such methods can further include processing the data for use in one or more applications and/or using the data as control input for an external device. Aspects of the invention may also include computer-readable media containing instructions for use in performing one or more features of these methods and/or utilizing the footwear and systems described above.

Other aspects of the invention relate to a system that includes at least two articles of footwear, each having a sensor system as described above, with an electronic module connected thereto, where each electronic module is configured for communicating data received from the sensors to an external device. The system may use several communication modes. In one embodiment, each module communicates separately with the external device. In another embodiment, the modules are additionally or alternately configured to communicate with each other. In a further embodiment, one electronic module is configured to transmit the data to the other electronic module, and the other electronic module is configured to transmit the data from both electronic modules to the external device.

Still other features and advantages of the invention will be apparent from the following specification taken in conjunction with the following drawings.

BRIEF DESCRIPTION OF THE DRAWINGS

FIG. 7 is a side cross-sectional view of a sole of a shoe incorporating the sensor system of FIG. 3, including an external output port;

FIG. 8 is a top view of a sole of a shoe incorporating another embodiment of a sensor system utilizing force-sensitive resistor (FSR) sensors;

FIGS. 9 and 10 are schematic views illustrating force-sensitive resistive behavior of a force-sensitive resistive material;

FIGS. 11-14 are side cross-sectional exploded views of soles of a shoe incorporating embodiments of sensor systems utilizing force-sensitive resistor (FSR) sensors;

FIGS. 16-20 are side cross-sectional exploded views of soles of a shoe incorporating embodiments of sensor systems utilizing separate electrodes and a force-sensitive resistive element;

FIG. 21 is a side view of a shoe incorporating another embodiment of a sensor system in an upper of the shoe;

FIG. 22 is a side cross-sectional exploded view of a sole of a shoe showing interchanging of two electronic modules;

DETAILED DESCRIPTION

Figure 1:
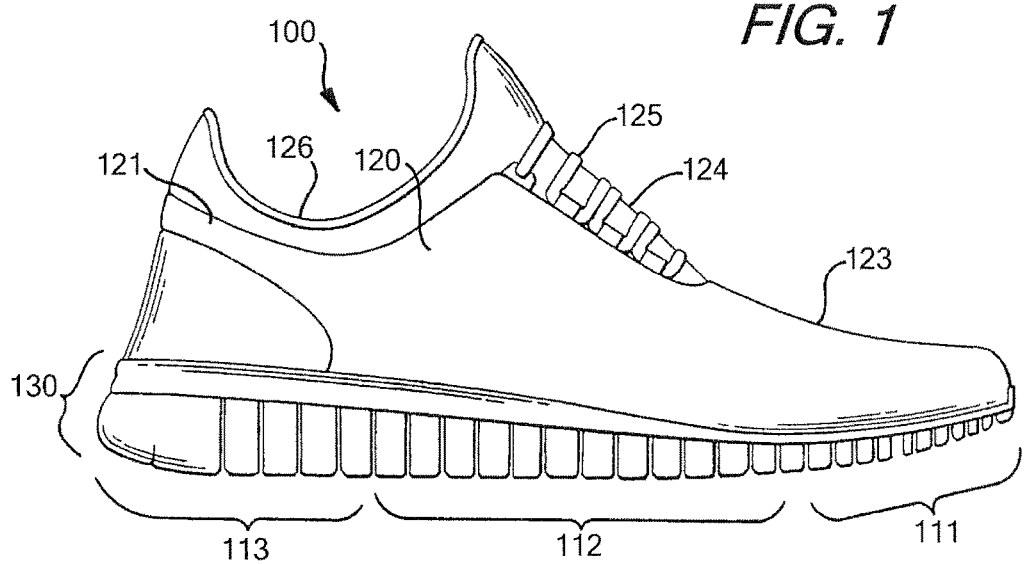
FIG. 1 is a side view of a shoe.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

Figure 2:
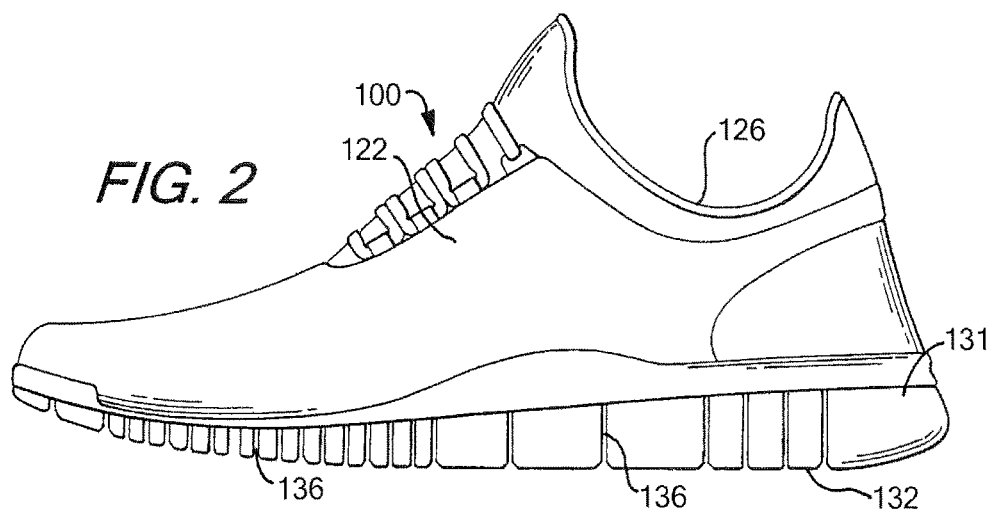
FIG. 2 is an opposed side view of the shoe of FIG. 1.

Footwear, such as a shoe, is shown as an example in FIGS. 1-2 and generally designated with the reference numeral 100. The footwear 100 can take many different forms, including, for example, various types of athletic footwear. In one exemplary embodiment, the shoe 100 generally includes a force sensor system 12 operably connected to a universal communication port 14. As described in greater detail below, the sensor system 12 collects performance data relating to a wearer of the shoe 100. Through connection to the universal communication port 14, multiple different users can access the performance data for a variety of different uses as described in greater detail below.

An article of footwear 100 is depicted in FIGS. 1-2 as including an upper 120 and a sole structure 130. For purposes of reference in the following description, footwear 100 may be divided into three general regions: a forefoot region 111, a midfoot region 112, and a heel region 113, as illustrated in FIG. 1. Regions 111-113 are not intended to demarcate precise areas of footwear 100. Rather, regions 111-113 are intended to represent general areas of footwear 100 that provide a frame of reference during the following discussion. Although regions 111-113 apply generally to footwear 100, references to regions 111-113 also may apply specifically to upper 120, sole structure 130, or individual components included within and/or formed as part of either upper 120 or sole structure 130.

As further shown in FIGS. 1 and 2, the upper 120 is secured to sole structure 130 and defines a void or chamber for receiving a foot. For purposes of reference, upper 120 includes a lateral side 121, an opposite medial side 122, and a vamp or instep area 123. Lateral side 121 is positioned to extend along a lateral side of the foot (i.e., the outside) and generally passes through each of regions 111-113. Similarly, medial side 122 is positioned to extend along an opposite medial side of the foot (i.e., the inside) and generally passes through each of regions 111-113. Vamp area 123 is positioned between lateral side 121 and medial side 122 to correspond with an upper surface or instep area of the foot. Vamp area 123, in this illustrated example, includes a throat 124 having a lace 125 or other desired closure mechanism that is utilized in a conventional manner to modify the dimensions of upper 120 relative the foot, thereby adjusting the fit of footwear 100. Upper 120 also includes an ankle opening 126 that provides the foot with access to the void within upper 120. A variety of materials may be used for constructing upper 120, including materials that are conventionally utilized in footwear uppers. Accordingly, upper 120 may be formed from one or more portions of leather, synthetic leather, natural or synthetic textiles, polymer sheets, polymer foams, mesh textiles, felts, non-woven polymers, or rubber materials, for example. The upper 120 may be formed from one or more of these materials wherein the materials or portions thereof are stitched or adhesively bonded together, e.g., in manners that are conventionally known and used in the art.

Upper 120 may also include a heel element (not shown) and a toe element (not shown). The heel element, when present, may extend upward and along the interior surface of upper 120 in the heel region 113 to enhance the comfort of footwear 100. The toe element, when present, may be located in forefoot region 111 and on an exterior surface of upper 120 to provide wear-resistance, protect the wearer's toes, and assist with positioning of the foot. In some embodiments, one or both of the heel element and the toe element may be absent, or the heel element may be positioned on an exterior surface of the upper 120, for example. Although the configuration of upper 120 discussed above is suitable for footwear 100, upper 120 may exhibit the configuration of any desired conventional or non-conventional upper structure without departing from this invention.

Sole structure 130 is secured to a lower surface of upper 120 and may have a generally conventional shape. The sole structure 130 may have a multipiece structure, e.g., one that includes a midsole 131, an outsole 132, and a foot contacting member 133, which may be a sockliner, a strobel, an insole member, a bootie element, a sock, etc. (See FIGS. 4-5). In the embodiment shown in FIGS. 4-5, the foot contacting member 133 is an insole member. The term "foot contacting member," as used herein does not necessarily imply direct contact with the user's foot, as another element may interfere with direct contact. Rather, the foot contacting member forms a portion of the inner surface of the foot-receiving chamber of an article of footwear. For example, the user may be wearing a sock that interferes with direct contact. As another example, the sensor system 12 may be incorporated into an article of footwear that is designed to slip over a shoe or other article of footwear, such as an external bootie element or shoe cover. In such an article, the upper portion of the sole structure may be considered a foot contacting member, even though it does not directly contact the foot of the user.

Midsole member 131 may be an impact attenuating member. For example, the midsole member 131 may be formed of polymer foam material, such as polyurethane, ethylvinylacetate, or other materials (such as phylon, phylite, etc.) that compress to attenuate ground or other contact surface reaction forces during walking, running, jumping, or other activities. In some example structures according to this invention, the polymer foam material may encapsulate or include various elements, such as a fluid-filled bladder or moderator, that enhance the comfort, motion-control, stability, and/or ground or other contact surface reaction force attenuation properties of footwear 100. In still other example structures, the midsole 131 may include additional elements that compress to attenuate ground or other contact surface reaction forces. For instance, the midsole may include column type elements to aid in cushioning and absorption of forces.

Outsole 132 is secured to a lower surface of midsole 131 in this illustrated example footwear structure 100 and is formed of a wear-resistant material, such as rubber or a flexible synthetic material, such as polyurethane, that contacts the ground or other surface during ambulatory or other activities. The material forming outsole 132 may be manufactured of suitable materials and/or textured to impart enhanced traction and slip resistance. The structure and methods of manufacturing the outsole 132 will be discussed further below. A foot contacting member 133 (which may be an insole member, a sockliner, a bootie member, a strobel, a sock, etc.) is typically a thin, compressible member that may be located within the void in upper 120 and adjacent to a lower surface of the foot (or between the upper 120 and midsole 131) to enhance the comfort of footwear 100. In some arrangements, an insole or sockliner may be absent, and in other embodiments, the footwear 100 may have a foot contacting member positioned on top of an insole or sockliner.

The outsole 132 shown in FIGS. 1 and 2 includes a plurality of incisions or sipes 136 in either or both sides of the outsole 132. These sipes 136 may extend from the bottom of the outsole 132 to an upper portion thereof or to the midsole 131. In one arrangement, the sipes 136 may extend from a bottom surface of the outsole 132 to a point halfway between the bottom of the outsole 132 and the top of the outsole 132. In another arrangement, the sipes 136 may extend from the bottom of the outsole 132 to a point greater than halfway to the top of the outsole 132. In yet another arrangement, the sipes 136 may extend from the bottom of the outsole 132 to a point where the outsole 132 meets the midsole 131. The sipes 136 may provide additional flexibility to the outsole 132, and thereby allow the outsole to more freely flex in the natural directions in which the wearer's foot flexes. In addition, the sipes 136 may aid in providing traction for the wearer. It is understood that embodiments of the present invention may be used in connection with other types and configurations of shoes, as well as other types of footwear and sole structures.

Figure 3:
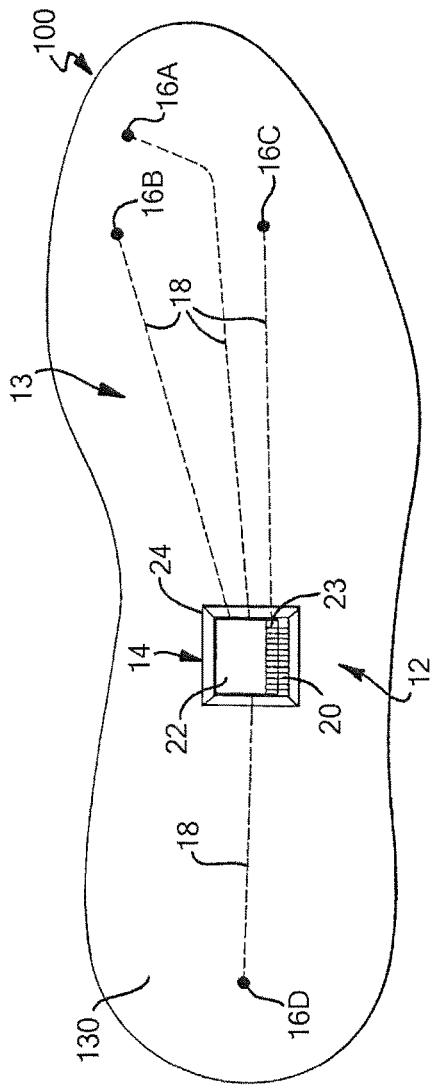
FIG. 3 is a top view of a sole of a shoe incorporating one embodiment of a sensor system.
Figure 4:
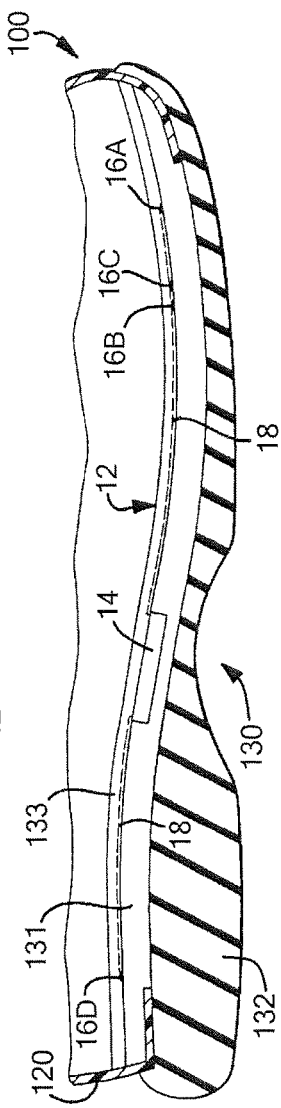
FIG. 4 is a side cross-sectional view of a shoe incorporating the sensor system of FIG. 3.
Figure 5:
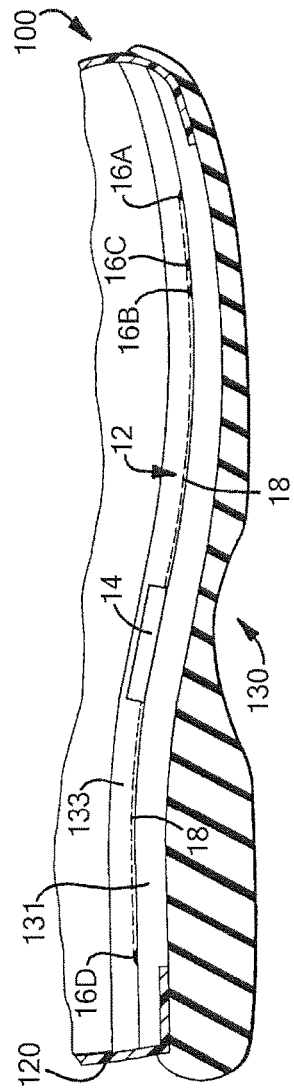
FIG. 5 is a side cross-sectional view of another shoe incorporating the sensor system of FIG. 3.

FIGS. 3-5 illustrate exemplary embodiments of the footwear 100 incorporating a sensor system 12 in accordance with the present invention. The sensor system 12 includes a force sensor assembly 13, having a plurality of sensors 16, and a communication or output port 14 in communication with the sensor assembly 13 (e.g., electrically connected via conductors). In the embodiment illustrated in FIG. 3, the system 12 has four sensors 16: a first sensor 16A at the big toe (first phalange) area of the shoe, two sensors 16B-C at the forefoot area of the shoe, including a second sensor 16B at the first metatarsal head region and a third sensor 16C at the fifth metatarsal head region, and a fourth sensor 16D at the heel. These areas of the foot typically experience the greatest degree of pressure during movement. The embodiment described below and shown in FIGS. 27-28 utilizes a similar configuration of sensors 16. Each sensor 16 is configured for detecting a force exerted by a user's foot on the sensor 16. The sensors communicate with the port 14 through sensor leads 18, which may be wire leads and/or another electrical conductor or suitable communication medium. For example, in one embodiment, the sensor leads 18 may be an electrically conductive medium printed on the insole member 133, the midsole member 131, or another member of the sole structure 130, such as a layer between the foot contacting member 133 and the midsole member 131.

Other embodiments of the sensor system 12 may contain a different number or configuration of sensors 16, such as the embodiments described below and shown in FIGS. 8, 11-21, and 27-28 and generally include at least one sensor 16. For example, in one embodiment, the system 12 includes a much larger number of sensors, and in another embodiment, the system 12 includes two sensors, one in the heel and one in the forefoot of the shoe 100. In addition, the sensors 16 may communicate with the port 14 in a different manner, including any known type of wired or wireless communication, including Bluetooth and near-field communication. A pair of shoes may be provided with sensor systems 12 in each shoe of the pair, and it is understood that the paired sensor systems may operate synergistically or may operate independently of each other, and that the sensor systems in each shoe may or may not communicate with each other. The communication of the sensor systems 12 is described in greater detail below. It is understood that the sensor system 12 may be provided with computer programs/algorithms to control collection and storage of data (e.g., pressure data from interaction of a user's foot with the ground or other contact surface), and that these programs/algorithms may be stored in and/or executed by the sensors 16, the module 22, and/or the external device 110.

The sensor system 12 can be positioned in several configurations in the sole 130 of the shoe 100. In the examples shown in FIGS. 4-5, the port 14, the sensors 16, and the leads 18 can be positioned between the midsole 131 and the foot contacting member 133, such as by connecting the port 14, the sensors 16, and/or the leads 18 to the top surface of the midsole 131 or the bottom surface of the foot contacting member 133. A cavity or well 135 can be located in the midsole 131 (FIG. 4) or in the foot contacting member 133 (FIG. 5) for receiving an electronic module, as described below, and the port 14 may be accessible from within the well 135. In the embodiment shown in FIG. 4, the well 135 is formed by an opening in the upper major surface of the midsole 131, and in the embodiment shown in FIG. 5, the well 135 is formed by an opening in the lower major surface of the insole 133. The well 135 may be located elsewhere in the sole structure 130 in other embodiments. For example, the well 135 may be located partially within both the foot contacting member 133 and the midsole member 131 in one embodiment, or the well 135 may be located in the lower major surface of the midsole 131 or the upper major surface of the insole 133. In a further embodiment, the well 135 may be located in the outsole 132 and may be accessible from outside the shoe 100, such as through an opening in the side, bottom, or heel of the sole 130. In the configurations illustrated in FIGS. 4-5, the port 14 is easily accessible for connection or disconnection of an electronic module, as described below. In other embodiments, the sensor system 12 can be positioned differently. For example, in one embodiment, the port 14, the sensors 16, and/or the leads 18 can be positioned within the outsole 132, midsole 131, or insole 133. In one exemplary embodiment, the port 14, the sensors 16, and/or the leads 18 may be positioned within a foot contacting member 133 positioned above the insole 133, such as a sock, sockliner, interior footwear bootie, or other similar article. In a further embodiment, the port 14, the sensors 16, and/or the leads 18 can be formed into an insert or a liner, designed to be quickly and easily insertable between the foot contacting member 133 and the midsole 131, such as shown in FIGS. 12 and 19-20. Still other configurations are possible, and some examples of other configurations are described below. As discussed, it is understood that the sensor system 12 may be included in each shoe in a pair.

In one embodiment, the sensors 16 are force sensors for measuring compression of the sole 130 and/or force on the sole 130. For example, the sensors 16 may be force-sensitive resistor (FSR) sensors or other sensors utilizing a force-sensitive resistive material (such as a quantum tunneling composite, a custom conductive foam, or a force-transducing rubber, described in more detail below), magnetic resistance sensors, piezoelectric or piezoresistive sensors, strain gauges, spring based sensors, fiber optic based sensors, polarized light sensors, mechanical actuator based sensors, displacement based sensors, and any other types of known sensors or switches capable of measuring compression of the foot contacting member 133, midsole 131, outsole 132, etc. A sensor may be an analog device or other device that measures force quantitatively, or it may simply be a binary-type ON/OFF switch (e.g., a silicone membrane type switch). It is understood that quantitative measurements of force by the sensors may include gathering and transmitting data that can be converted into quantitative force measurements by an electronic device, such as the module 22 or the external device 110. Some sensors as described herein, such as piezo sensors, force-sensitive resistor sensors, quantum tunneling composite sensors, custom conductive foam sensors, etc., can measure differences or changes in resistance, capacitance, or electric potential and translate the measured differential to a force component. A spring-based sensor, as mentioned above, can be configured to measure deformation or change of resistance caused by pressure and/or deformation. A fiber optic based sensor, as described above, contains compressible tubes with a light source and a light measurement device connected thereto. In such a sensor, when the tubes are compressed, the wavelength of light within the tubes changes, and the measurement device can detect such changes and translate the changes into a force measurement. Nanocoatings could also be used, such as a midsole dipped into conductive material. Polarized light sensors could be used, wherein changes in light transmission properties are measured and correlated to the pressure or force exerted on the sole. One embodiment utilizes a multiple array (e.g. 100) of binary on/off sensors, and force components can be detected by "puddling" of sensor signals in specific areas. Still other types of sensors not mentioned herein may be used. It is understood that the sensors can be relatively inexpensive and capable of being placed in shoes in a mass-production process. More complex sensor systems that may be more expensive could be incorporated in a training type shoe.

Additionally, the sensors 16 may be placed or positioned in engagement with the shoe structure in many different manners. In one example, the sensors 16 may be printed conductive ink sensors, electrodes, and/or leads deposited on a sole member, such as an airbag or other fluid-filled chamber, a foam material, or another material for use in the shoe 100, or a sock, bootie, insert, liner, insole, midsole, etc. The sensors 16 and/or leads 18 may be woven into garment or fabric structures (such as sockliners, booties, uppers, inserts, etc.), e.g., using conductive fabric or yarns when weaving or knitting the garment or fabric structures. Many embodiments of the sensor system 12 can be made inexpensively, for example, by using a force-sensitive resistor sensor or a force-sensitive resistive material, as described below and shown in FIGS. 8 and 11-21. It is understood that the sensors 16 and/or leads 18 also may be deposited on or engaged with a portion of the shoe structure in any desired manner, such as by conventional deposition techniques, by conductive nano-coating, by conventional mechanical connectors, and any other applicable known method. The sensor system can also be configured to provide mechanical feedback to the wearer. Additionally, the sensor system 12 may include a separate power lead to supply power to the sensors 16. In the embodiments described below and shown in FIGS. 5A-5E and FIGS. 27-28, the sensor system 12, 1312 includes a separate power lead 18A, 1318A that is used to connect the sensors 16, 1316 to the port 14, 14A-E to supply power from the module 22 to the sensors 16, 1316. As a further example, the sensor system 12 can be made by incorporating printed conductive ink sensors 16 or electrodes and conductive fabric or yarn leads 18, or forming such sensors on the foam or airbag of a shoe. Sensors 16 could be incorporated onto or into an airbag in a variety of manners. In one embodiment, the sensors 16 could be made by printing a conductive, force-sensitive material on the airbag on one or more surfaces of the airbag to achieve a strain gauge-like effect. When the bag surfaces expand and/or contract during activity, the sensors can detect such changes through changes in resistance of the force-sensitive material to detect the forces on the airbag. In a bag having internal fabrics to maintain a consistent shape, conductive materials can be located on the top and bottom of the airbag, and changes in the capacitance between the conductive materials as the bag expands and compresses can be used to determine force. Further, devices that can convert changes in air pressure into an electrical signal can be used to determine force as the airbag is compressed.

Figure 6:
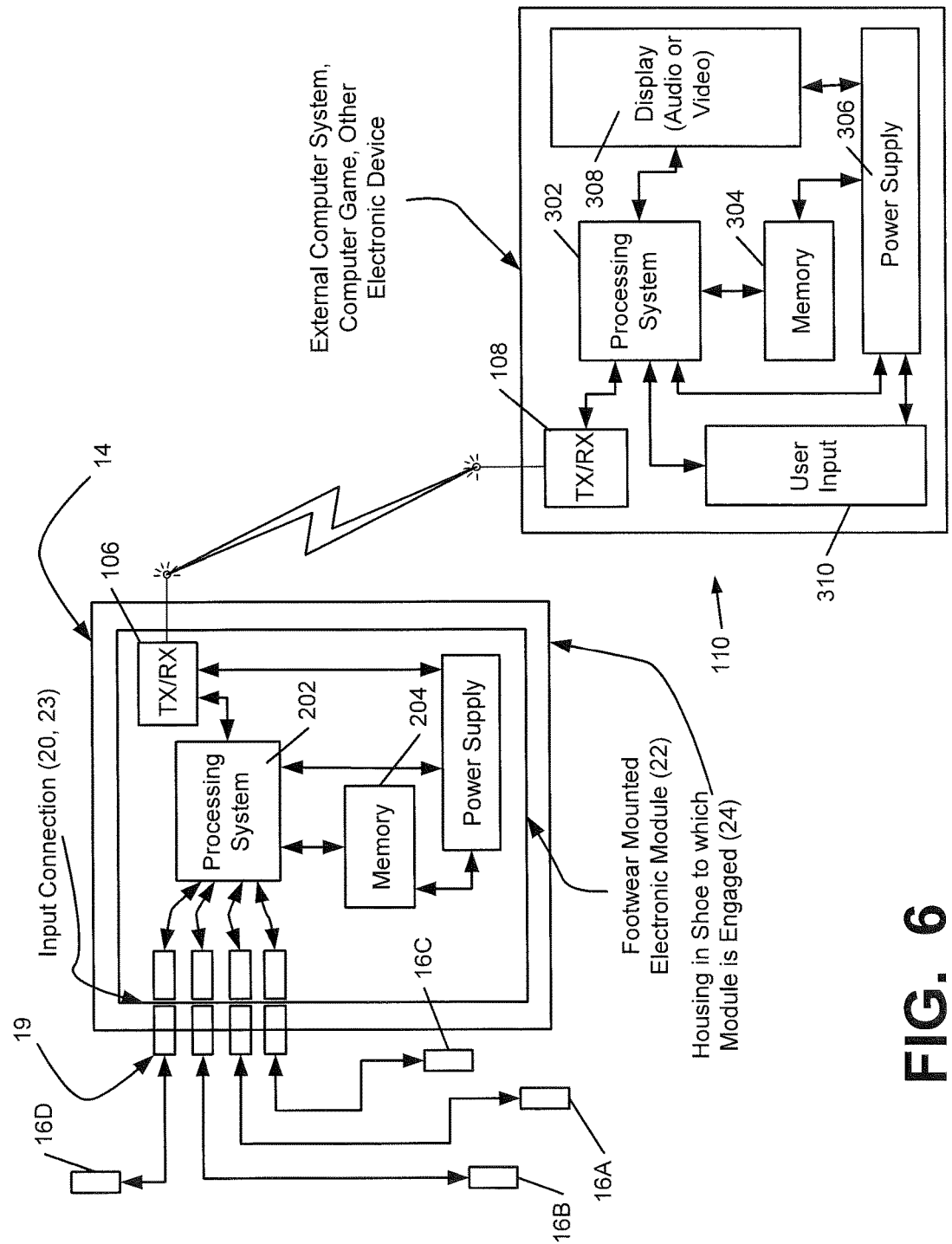
FIG. 6 is a schematic diagram of one embodiment of an electronic module capable of use with a sensor system, in communication with an external electronic device.

The port 14 is configured for communication of data collected by the sensors 16 to an outside source, in one or more known manners. In one embodiment, the port 14 is a universal communication port, configured for communication of data in a universally readable format. In the embodiments shown in FIGS. 3-5, the port 14 includes an interface 20 for connection to an electronic module 22, shown in connection with the port 14 in FIG. 3. In the embodiment shown in FIGS. 3-5, the interface 20 takes the form of electrical contacts. Additionally, in this embodiment, the port 14 is associated with a housing 24 for insertion of the electronic module 22, located in the well 135 in the middle arch or midfoot region of the article of footwear 100. The positioning of the port 14 in FIGS. 3-5 not only presents minimal contact, irritation, or other interference with the user's foot, but also provides easy accessibility by simply lifting the insole 133. Additionally, as illustrated in FIG. 6, the sensor leads 18 also form a consolidated interface at their terminal ends, in order to connect to the port 14. In one embodiment, the consolidated interface may include individual connection of the sensor leads 18 to the port interface 20, such as through a plurality of electrical contacts. In another embodiment, the sensor leads 18 could be consolidated to form an external interface 19, such as a plug-type interface as described below, or in another manner, and in a further embodiment, the sensor leads 18 may form a non-consolidated interface, with each lead 18 having its own sub-interface. As illustrated in FIG. 6, the sensor leads 18 can converge to a single location to form the consolidated interface. As also described below, the module 22 may have an interface 23 for connection to the port interface 20 and/or the sensor leads 18.

The port 14 is adapted for connection to a variety of different electronic modules 22, which may be as simple as a memory component (e.g., a flash drive) or which may contain more complex features. It is understood that the module 22 could be as complex a component as a personal computer, mobile device, server, etc. The port 14 is configured for transmitting data gathered by the sensors 16 to the module 22 for storage and/or processing. Examples of a housing and electronic modules in a footwear article are illustrated in U.S. patent application Ser. No. 11/416,458, published as U.S. Patent Application Publication No. 2007/0260421, which is incorporated by reference herein and made part hereof. Although the port 14 is illustrated with electronic contacts forming an interface 20 for connection to a module, in other embodiments, the port 14 may contain one or more additional or alternate communication interfaces. For example, the port 14 may contain or comprise a USB port, a Firewire port, 16-pin port, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique.

The sensor leads 18 may be connected to the port 14 in a variety of different configurations. FIGS. 5A-5E illustrate example embodiments of a port 14A-E positioned within a well 135 in an article of footwear 100, such as within a sole member of the sole structure 130 as described above. In the embodiments shown in FIGS. 5A-5E, the well 135 has a plurality of walls, including side walls 139 and a base wall 143.

Figure 5A:
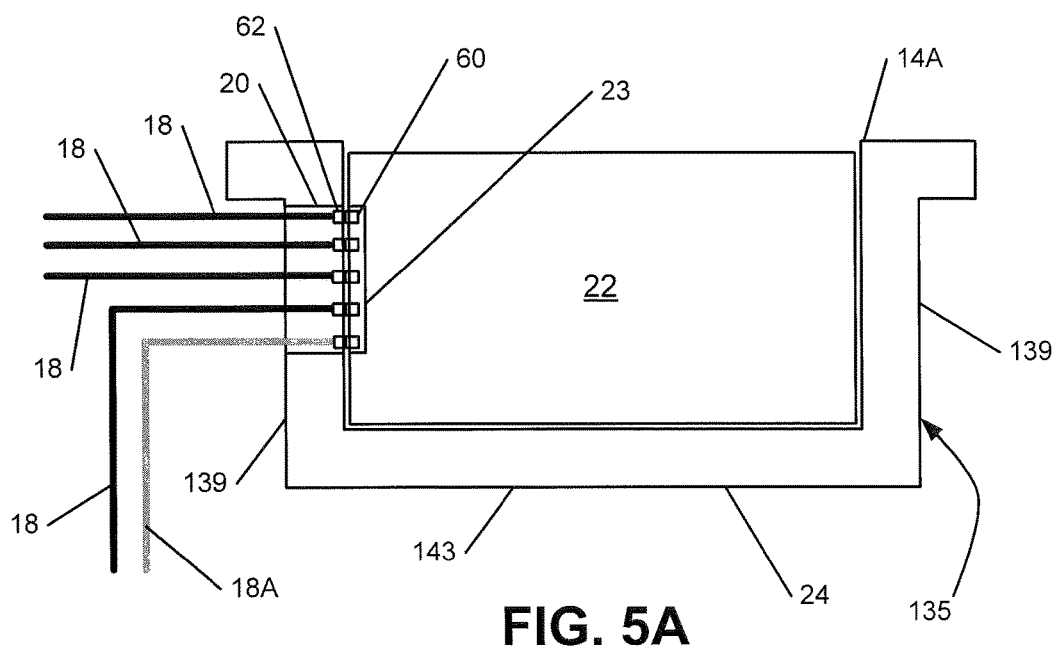
FIG. 5A is a side cross-sectional view of one embodiment of a port located in a well in a sole of an article of footwear.

FIG. 5A illustrates an embodiment of the port 14A where four sensor leads 18 and a power lead 18A are connected to the port 14A through a single side wall 139 of the well 135. In the embodiment illustrated, the sensor leads 18 form a consolidated interface in the form of a 5-pin connection, that is connected to an interface 20 of the port 14A. In this configuration, the leads 18, 18A are connected to the port interface 20 to form a consolidated interface, and each of the leads 18, 18A terminates in a connection pin 62 to form a multi-pin connection. This connection pin 62 can be considered an exposed end of the lead 18, 18A accessible within the well 135, in one embodiment. Likewise, the module 22 has a connection 23 that includes five pin connections 60 for connection to the connection pins 62 of the leads 18, 18A in the port interface 20.

Figure 5B:
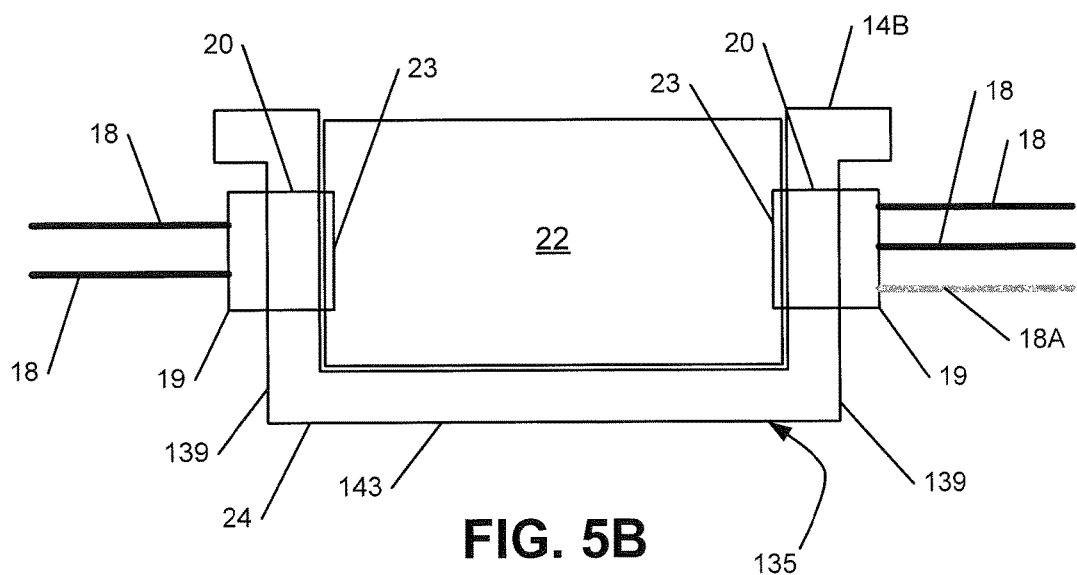
FIG. 5B is a side cross-sectional view of a second embodiment of a port located in a well in a sole of an article of footwear.

FIG. 5B illustrates an embodiment of the port 14B where two sensor leads 18 are connected to the port 14B through one of the side walls 139 of the well 135 and two other sensor leads 18 and a power lead 18A are connected to the port 14B through another one of the side walls 139. In this embodiment, the leads 18 form two separate consolidated lead interfaces 19, in the form of external interfaces 19, and the port 14B has two separate interfaces 20 for connection to the leads 18, 18A. The external interfaces 19 may be plug-type interfaces, pin-type interfaces, or other interfaces, and the port interfaces 20 are complementarily configured to connect to the external lead interfaces 19. Further, in this configuration, the module 22 has two interfaces 23 that are configured for connection to the port interfaces 20.

Figure 5C:
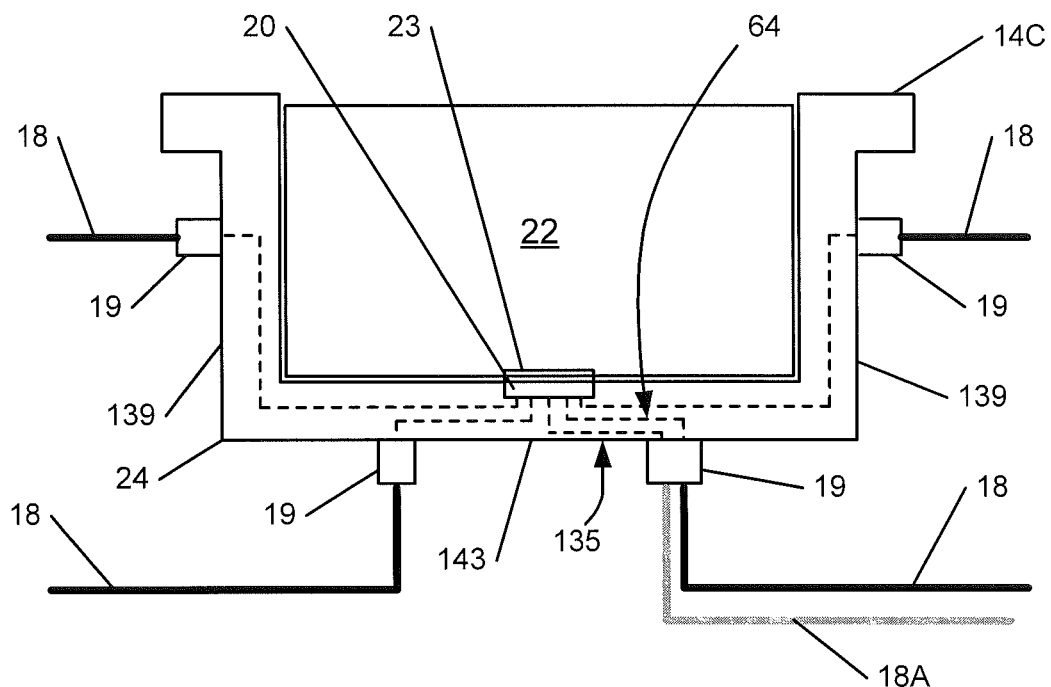
FIG. 5C is a side cross-sectional view of a third embodiment of a port located in a well in a sole of an article of footwear.

FIG. 5C illustrates an embodiment of the port 14C where the sensor leads 18 and the power lead 18A are connected to the port 14C through the side walls 139 and through the base wall 143 of the well 135. In this embodiment, the sensor leads 18 form several separate lead interfaces 19 for connection to the port 14C. The port 14C includes internal circuitry 64 that consolidates the connections of all the leads 18, 18A to the port interface 20, for connection to the module interface 23. The port 14C may further include complementary interfaces for connection to each of the lead interfaces 19. It is understood that the leads 18, 18A may be connected through one or more of the side walls 139 of the well 135 in this embodiment, and that the leads 18, 18A are shown connected through two of the side walls 139 for illustrative purposes. It is also understood that in this embodiment, more than one lead 18, 18A may be connected through a particular side wall 139 of the well 135, and that only one lead 18, 18A may be connected through the base wall 143.

Figure 5D:
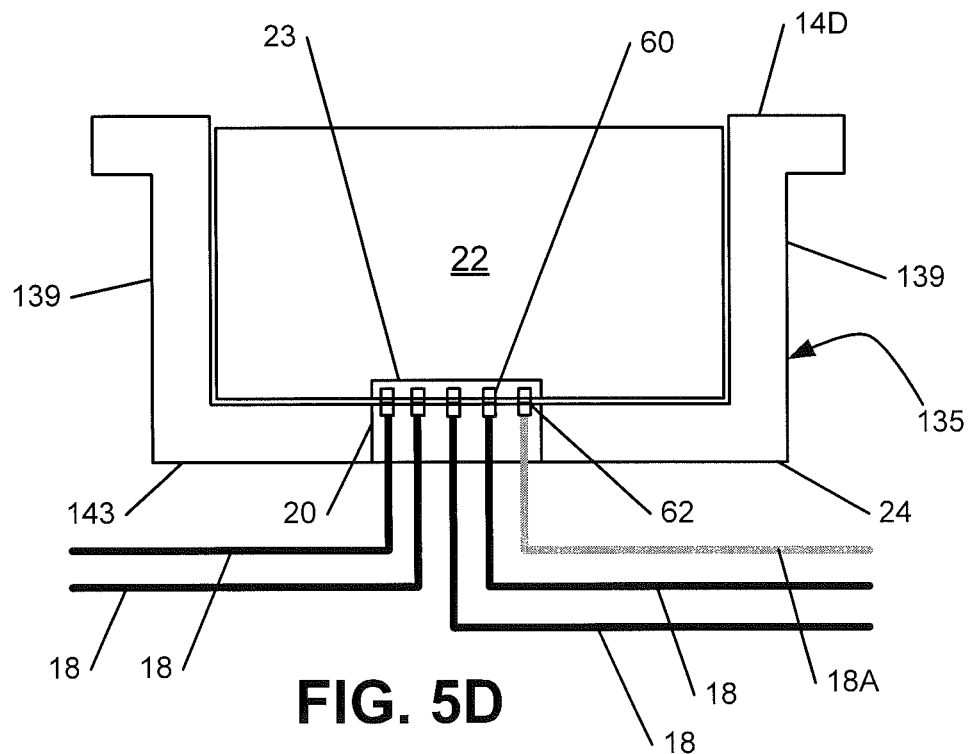
FIG. 5D is a side cross-sectional view of a fourth embodiment of a port located in a well in a sole of an article of footwear.

FIG. 5D illustrates an embodiment of the port 14D where four sensor leads 18 and a power lead 18A are connected to the port 14D through the base wall 143 of the well 135. In the embodiment illustrated, the leads 18, 18A form a consolidated interface that is connected to an interface 20 at the bottom of the port 14D, in a similar configuration to the connections described above and shown in FIG. 5A. Each of the leads 18, 18A terminates in a connection pin 62 at the port interface 20, and the module interface 23 includes a plurality of pin connections 60 configured for connection to the connection pins 62 of the leads 18, 18A.

Figure 5E:
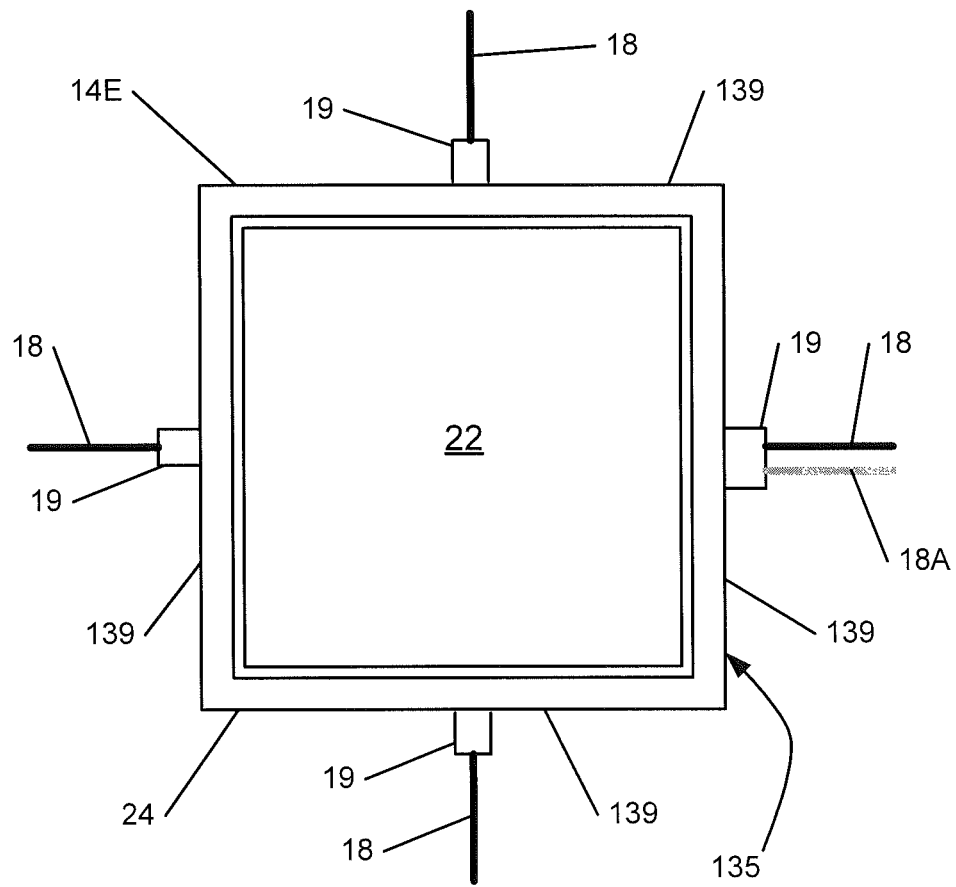
FIG. 5E is a top view of a fifth embodiment of a port located in a well in a sole of an article of footwear.

FIG. 5E illustrates an embodiment of the port 14E where four sensor leads 18 and a power lead 18A are connected to the port 14E through each of four side walls 139 of the well 135. In this embodiment, the leads 18, 18A form several separate interfaces 19 for connection to the port 14E, similar to the embodiment described above and shown in FIG. 5C. As described above, the port 14E may include complementary interfaces for connection to the lead interfaces 19, and may also include an interface for connection to the module 22. In other embodiments, the leads 18, 18A can be connected through any number of side walls 139 of the well 135.

In embodiments such as those illustrated in FIGS. 5B, 5C, and 5E, where the sensors 18 form more than one interface 19, the port 14B, 14C, 14E and/or the module 22 may have multiple interfaces 20, 23, or may have only a single interface 20, 23, and the port 14 may have internal circuitry 64 to connect all of the leads 18, 18A to the interfaces 20, 23. Additionally, the module 22 may have one or more interfaces 23 that are complementary to the interface(s) 20 of the port 14, for connection thereto. For example, if the port 14 has interface(s) 20 in the side walls 139 and/or base wall 143 thereof, the module 22 may have complementary interface(s) 23 in the side walls and/or base wall as well. It is understood that the module 22 and the port 14 may not have identically complementary interfaces 20, 23, and that only one pair of complementary interfaces 20, 23 may be able to achieve communication between the components. In other embodiments, the port 14 and the well 135 may have a different configuration for connection of the leads 18, 18A. Additionally, the port 14 may have a different shape, which may enable a greater variety of connection configurations. Further, any of the connection configurations described herein, or combinations thereof, can be utilized with the various embodiments of sensor systems described herein.

The module 22 may additionally have one or multiple communication interfaces for connecting to an external device 110 to transmit the data for processing, as described below and shown in FIG. 6. Such interfaces can include any of the contacted or contactless interfaces described above. In one example, the module 22 includes at least a retractable USB connection for connection to a computer. In another example, the module 22 may be configured for contacted or contactless connection to a mobile device, such as a watch, cell phone, portable music player, etc. The module 22 may be configured to be removed from the footwear 100 to be directly connected to the external device 110 for data transfer, such as by the retractable USB connection described above. However, in another embodiment, the module 22 may be configured for wireless communication with the external device 110, which allows the device 22 to remain in the footwear 100. In a wireless embodiment, the module 22 may be connected to an antenna for wireless communication. The antenna may be shaped, sized, and positioned for use with the appropriate transmission frequency for the selected wireless communication method. Additionally, the antenna may be located internally within the module 22 or external to the module. In one example, the sensor system 12 itself (such as the leads 18 and conductive portions of the sensors 16) could be used to form an antenna. In one embodiment, the module 22 may be permanently mounted within the footwear 100, or alternately may be removable at the option of the user and capable of remaining in the footwear 100 if desired. Additionally, as further explained below, the module 22 may be removed and replaced with another module 22 programmed and/or configured for gathering and/or utilizing data from the sensors 16 in another manner. If the module 22 is permanently mounted within the footwear 100, the sensor system 12 may further contain an external port 15 to allow for data transfer and/or battery charging, such as a USB or Firewire port, as shown in FIG. 7. It is understood that the module 22 may be configured for both contacted and contactless communication.

While the port 14 may be located in a variety of positions without departing from the invention, in one embodiment, the port 14 is provided at a position and orientation and/or is otherwise structured so as to avoid or minimize contact with and/or irritation of the wearer's foot, e.g., as the wearer steps down in and/or otherwise uses the article of footwear 100, such as during an athletic activity. The positioning of the port 14 in FIGS. 3-5 illustrates one such example. In another embodiment, the port 14 is located proximate the heel or instep regions of the shoe 100. Other features of the footwear structure 100 may help reduce or avoid contact between the wearer's foot and the port 14 (or an element connected to the port 14) and improve the overall comfort of the footwear structure 100. For example, as illustrated in FIGS. 4-5, the insole 133, or other foot contacting member, may fit over and at least partially cover the port 14, thereby providing a layer of padding between the wearer's foot and the port 14. Additional features for reducing contact between and modulating any undesired feel of the port 14 at the wearer's foot may be used. Of course, if desired, the opening to the port 14 may be provided through the top surface of the insole member 133 without departing from the invention. Such a construction may be used, for example, when the housing 24, electronic module 22, and other features of the port 14 include structures and/or are made from materials so as to modulate the feel at the user's foot, when additional comfort and feel modulating elements are provided, etc. Any of the various features described above that help reduce or avoid contact between the wearer's foot and a housing (or an element received in the housing) and improve the overall comfort of the footwear structure may be provided without departing from this invention, including the various features described above in conjunction with FIGS. 4-5, as well as other known methods and techniques.

In one embodiment, where the port 14 is configured for contacted communication with a module 22 contained in a well 135 in the sole structure 130, the port 14 is positioned within or immediately adjacent the well 135, for connection to the module 22. It is understood that if the well 135 further contains a housing 24 for the module 22, the housing 22 may be configured for connection to the port 14, such as by providing physical space for the port 14 or by providing hardware for interconnection between the port 14 and the module 22. The positioning of the port 14 in FIG. 3 illustrates one such example, where the housing 24 provides physical space to receive the port 14 for connection to the module 22.

FIG. 6 shows a schematic diagram of an example electronic module 22 including data transmission/reception capabilities through a data transmission/reception system 106, which may be used in accordance with at least some examples of this invention. While the example structures of FIG. 6 illustrate the data transmission/reception system (TX-RX) 106 as integrated into the electronic module structure 22, those skilled in the art will appreciate that a separate component may be included as part of a footwear structure 100 or other structure for data transmission/reception purposes and/or that the data transmission/reception system 106 need not be entirely contained in a single housing or a single package in all examples of the invention. Rather, if desired, various components or elements of the data transmission/reception system 106 may be separate from one another, in different housings, on different boards, and/or separately engaged with the article of footwear 100 or other device in a variety of different manners without departing from this invention. Various examples of different potential mounting structures are described in more detail below.

In the example of FIG. 6, the electronic component 22 may includes a data transmission/reception element 106 for transmitting data to and/or receiving data from one or more remote systems. In one embodiment, the transmission/reception element 106 is configured for communication through the port 14, such as by the contacted or contactless interfaces described above. In the embodiment shown in FIG. 6, the module 22 includes an interface 23 configured for connection to the port 14 and/or sensors 16. In the module 22 illustrated in FIG. 3, the interface 23 has contacts that are complementary with the contacts of the interface 20 of the port 14, to connect with the port 14. In other embodiments, as described above, the port 14 and the module 22 may contain different types of interfaces 20, 23, which may be wired or wireless. It is understood that in some embodiments, the module 22 may interface with the port 14 and/or sensors 16 through the TX-RX element 106. Accordingly, in one embodiment, the module 22 may be external to the footwear 100, and the port 14 may comprise a wireless transmitter interface for communication with the module 22. The electronic component 22 of this example further includes a processing system 202 (e.g., one or more microprocessors), a memory system 204, and a power supply 206 (e.g., a battery or other power source).

Connection to the one or more sensors can be accomplished through TX-RX element 106, but additional sensors (not shown) may be provided to sense or provide data or information relating to a wide variety of different types of parameters, such as physical or physiological data associated with use of the article of footwear 100 or the user, including pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, data regarding angular orientation and changes in angular orientation (such as a gyroscope-based sensor), etc., and this data may be stored in memory 204 and/or made available, for example, for transmission by the transmission/reception system 106 to some remote location or system. The additional sensor(s), if present, may also include an accelerometer (e.g., for sensing direction changes during steps, such as for pedometer type speed and/or distance information, for sensing jump height, etc.).

As additional examples, electronic modules, systems, and methods of the various types described above may be used for providing automatic impact attenuation control for articles of footwear. Such systems and methods may operate, for example, like those described in U.S. Pat. No. 6,430,843, U.S. Patent Application Publication No. 2003/0009913, and U.S. Patent Application Publication No. 2004/0177531, which describe systems and methods for actively and/or dynamically controlling the impact attenuation characteristics of articles of footwear (U.S. Pat. No. 6,430,843, U.S. Patent Application Publication No. 2003/0009913, and U.S. patent application Publication No. 2004/0177531 each are entirely incorporated herein by reference and made part hereof). When used for providing speed and/or distance type information, sensing units, algorithms, and/or systems of the types described in U.S. Pat. Nos. 5,724,265, 5,955,667, 6,018,705, 6,052,654, 6,876,947 and 6,882,955 may be used. These patents each are entirely incorporated herein by reference.

As further shown in FIG. 6, an electronic module 22 can include an activation system (not shown). The activation system or portions thereof may be engaged with the module 22 or with the article of footwear 100 (or other device) together with or separate from other portions of the electronic module 22. The activation system may be used for selectively activating the electronic module 22 and/or at least some functions of the electronic module 22 (e.g., data transmission/reception functions, etc.). A wide variety of different activation systems may be used without departing from this invention, and a variety of such systems will be described in more detail below with respect to various included figures. In one example, the sensor system 12 may be activated and/or deactivated by activating the sensors 16 in a specific pattern, such as consecutive or alternating toe/heel taps. In another example, the sensor system 12 may be activated by a button or switch, which may be located on the module 22, on the shoe 100, or on an external device in communication with the sensor system 12, as well as other locations. In any of these embodiments, the sensor system 12 may contain a "sleep" mode, which can deactivate the system 12 after a set period of inactivity. In an alternate embodiment, the sensor system 12 may operate as a low-power device that does not activate or deactivate.

The module 22 may further be configured for communication with an external device 110, which may be an external computer or computer system, mobile device, gaming system, or other type of electronic device, as shown in FIG. 6. The exemplary external device 110 shown in FIG. 6 includes a processor 302, a memory 304, a power supply 306, a display 308, a user input 310, and a data transmission/reception system 108. The transmission/reception system 108 is configured for communication with the module 22 via the transmission/reception system 106 of the module 22, through any type of known electronic communication, including the contacted and contactless communication methods described above and elsewhere herein. It is understood that the module 22 can be configured for communication with a plurality of external devices, including a wide variety of different types and configurations of electronic devices. Additionally, the transmission/reception system 106 of the module 22 may be configured for a plurality of different types of electronic communication. It is further understood that the shoe 100 may include a separate power source to operate the sensors 16 if necessary, such as a battery, piezoelectric, solar power supplies, or others. The sensors 16 may also simply receive power through connection to the module 22.

As described above, many different types of sensors can be incorporated into sensor systems according to the present invention. FIG. 8 illustrates one exemplary embodiment of a shoe 100 that contains a sensor system 212 that includes a sensor assembly 213 incorporating a plurality of force-sensitive resistor (FSR) sensors 216. The sensor system 212 is similar to the sensor system 12 described above, and also includes a port 14 in communication with an electronic module 22 and a plurality of leads 218 connecting the FSR sensors 216 to the port 14. The module 22 is contained within a well or cavity 135 in the sole structure 130 of the shoe 100, and the port 14 is connected to the well 135 to enable connection to the module 22 within the well 135. The port 14 and the module 22 include complementary interfaces 220, 223 for connection and communication.

The force-sensitive resistor shown in FIG. 8 contains first and second electrodes or electrical contacts 240, 242 and a force-sensitive resistive material 244 disposed between the electrodes 240, 242 to electrically connect the electrodes 240, 242 together. When pressure is applied to the force-sensitive material 244, the resistivity and/or conductivity of the force-sensitive material 244 changes, which changes the electrical potential between the electrodes 240, 242. The change in resistance can be detected by the sensor system 212 to detect the force applied on the sensor 216. The force-sensitive resistive material 244 may change its resistance under pressure in a variety of ways. For example, the force-sensitive material 244 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 244 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 244 and the electrode 240, 242 and/or the surface resistance between a conducting layer (e.g. carbon/graphite) and a force-sensitive layer (e.g. a semiconductor) of a multi-layer material 244. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 244, as defined herein, may be or include a doped or non-doped semiconducting material.

The electrodes 240, 242 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 218 can be connected to the electrodes 240, 242 by any suitable method, including welding, soldering, brazing, adhesively joining, fasteners, or any other integral or non-integral joining method. Alternately, the electrode 240, 242 and associated lead 218 may be formed of a single piece of the same material.

FIGS. 9-10 illustrate generally the use of a force-sensitive resistive material M in a sensor 16, such as the FSR sensors 216 shown in FIG. 8. The electrodes (+) and (−) have an electrical potential P1 between them, as shown in FIG. 9. When the force-sensitive resistive material M is compressed, the resistance of the material M changes, and thus, the potential P2 between the electrodes (+) and (−) changes, as shown in FIG. 10. The material M may utilize volume-based resistance, contact-based resistance, or other types of force-sensitive resistive behavior. For example, the force-sensitive resistive material 244 of the sensors 216 in FIG. 8 may behave in this manner. As another example, the quantum tunneling composite, custom conductive foam, force transducing rubber, and other force-sensitive resistive materials described below and shown in FIGS. 16-20 exhibit force-sensitive resistive behavior. It is understood that the electrodes (+) and (−) may be positioned in a different arrangement, such as in a sandwich arrangement with the material M positioned between the electrodes (+) and (−).

In the example embodiment shown in FIG. 8, the electrodes 240, 242 of the FSR sensor 216 have a plurality of interlocking or intermeshing fingers 246, with the force-sensitive resistive material 244 positioned between the fingers 246 to electrically connect the electrodes 240, 242 to each other. In the embodiment shown in FIG. 8, each of the leads 218 independently supplies power from the module 22 to the sensor 216 to which each respective lead 218 is connected. It is understood that the sensor leads 218 may include separate leads extending from each electrode 240, 242 to the port 14, and that the module 22 may provide electrical power to the electrodes 240, 242 through such separate leads, such as through a separate power lead 18A, 1318A as described elsewhere herein.

Force-sensitive resistors suitable for use in the sensor system 212 are commercially available from sources such as Sensitronics LLC. Embodiments of force-sensitive resistors which may be suitable for use are shown and described in U.S. Pat. Nos. 4,314,227 and 6,531,951, which are incorporated herein by reference in their entireties and made parts hereof.

Figure 27:
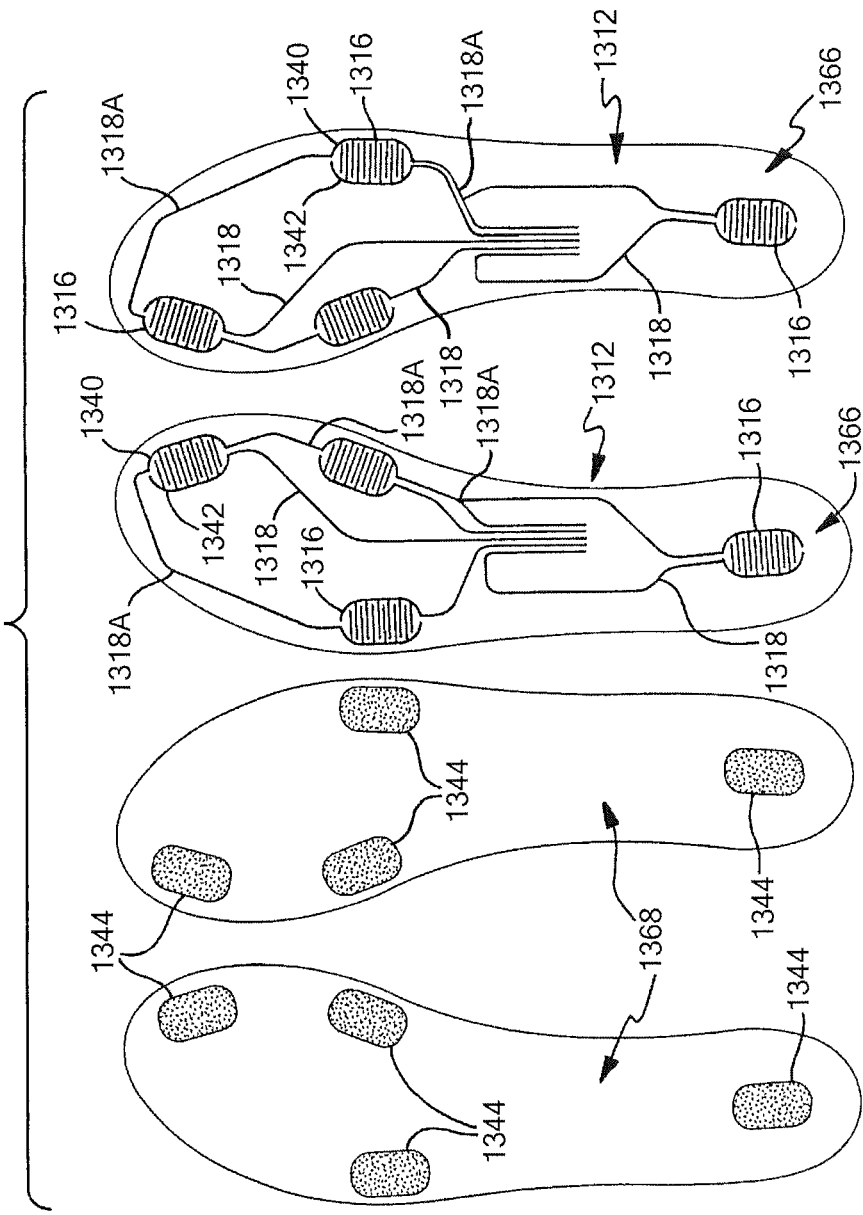
FIG. 27 is a top view of two sets of layers for use in constructing a sensor system.
Figure 28:
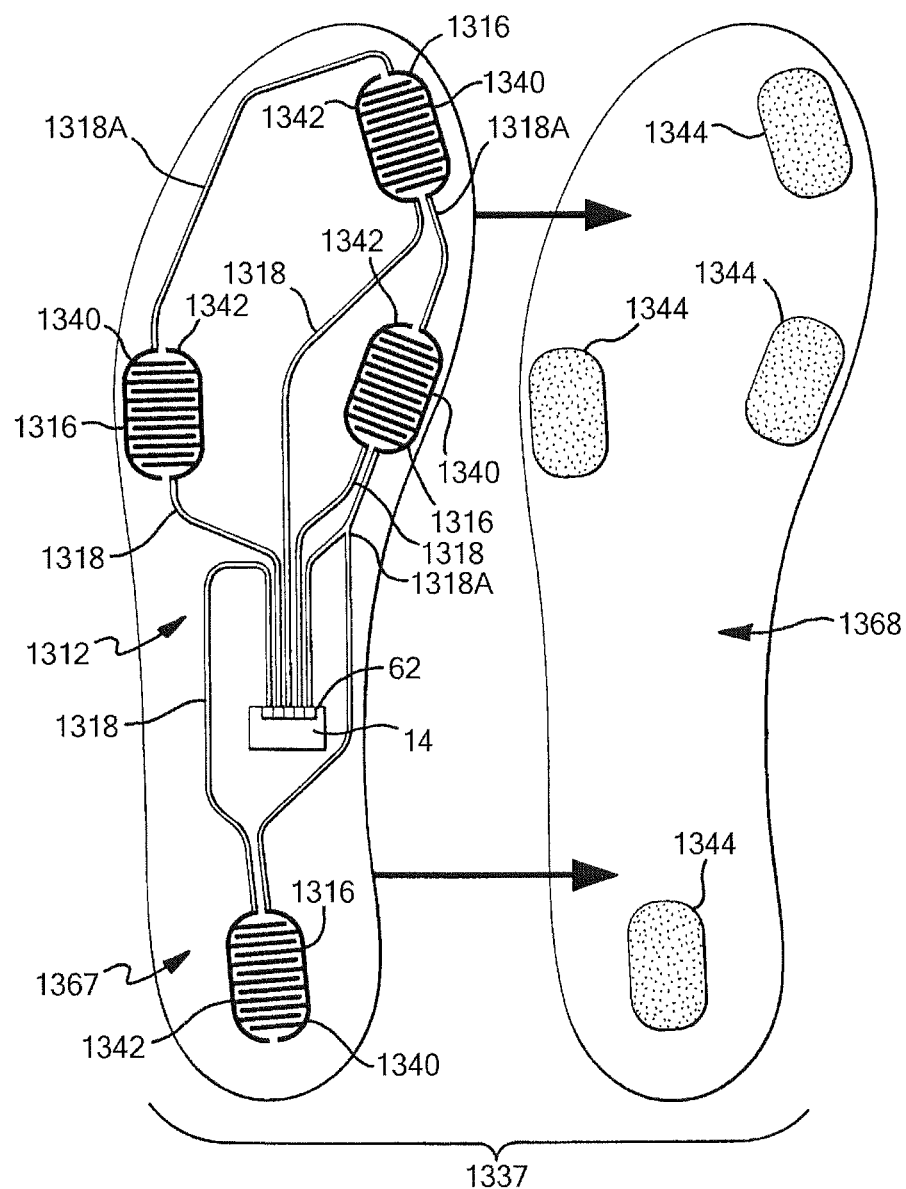
FIG. 28 is a top view of the assembly of an insert member containing a sensor system, using one set of layers as shown in FIG. 27.

FIGS. 27-28 illustrate another embodiment of an FSR sensor system 1312 for incorporation into an article of footwear 100. The sensor system 1312 includes four sensors 1316, with a first sensor 1316 positioned in the first phalange (big toe) area, a second sensor 1316 positioned in the first metatarsal head area, a third sensor 1316 positioned in the fifth metatarsal head area, and a fourth sensor 1316 positioned in the heel area, similarly to the configuration shown in FIG. 3. The sensors 1316 each have a sensor lead 1318 connecting the sensor 1316 to the port 14. Additionally, a power lead 1318A extends from the port 14 and is connected to all four sensors 1316 in series configuration to supply power to all four sensors 1316. Other configurations, including parallel configurations, are possible as well. As shown in FIG. 28, each of the leads 1318, 1318A are connected to the port 14 for connection and transfer of data to a module (not shown) connected to the port 14. It is understood that the port 14 may have any configuration described herein. In this embodiment, the leads 1318, 1318A are positioned suitably for a 5-pin connection as shown in FIG. 5A, with a plurality of connection pins 62.

Similarly to the system 212 described above with respect to FIG. 8, each sensor 1316 of the sensor system 1312 contains first and second electrodes or electrical contacts 1340, 1342 and a force-sensitive resistive material 1344 disposed between the electrodes 1340, 1342 to electrically connect the electrodes 1340, 1342 together. When pressure is applied to the force-sensitive material 1344, the resistivity and/or conductivity of the force-sensitive material 1344 changes, which changes the electrical potential between the electrodes 1340, 1342. The change in resistance can be detected by the sensor system 1312 to detect the force applied on the sensor 1316. Additionally, the FSR sensors 1316 each have a plurality of interlocking or intermeshing fingers 1346, with the force-sensitive resistive material 1344 positioned between the fingers 1346 to electrically connect the electrodes 1340, 1342 to each other.

In the embodiment of the sensor system 1312 shown in FIGS. 27-28, each sensor 1316 includes two contacts 1340, 1342 constructed of a conductive metallic layer and a carbon layer (such as carbon black) forming a contact surface on the metallic layer. The sensors 1316 also include a force-sensitive resistive material 1344 that also is constructed of a layer or puddle of carbon (such as carbon black), which is in contact with the carbon contact surface of the electrodes 1340, 1342. The carbon-on-carbon contact can produce greater conductivity changes under pressure, increasing the effectiveness of the sensors 1316. The leads 1318, 1318A in this embodiment are constructed of a conductive metallic material that may be the same as the material of the metallic layer of the contacts 1340, 1342. In one embodiment, the leads 1318, 1318A and the metallic layers of the contacts 1340, 1342 are constructed of silver.

As shown in FIGS. 27-28, in this example embodiment, the sensor system 1312 is constructed of two flexible layers 1366 and 1368 that combine to form an insert member 1337 for insertion into an article of footwear, such as between the foot contacting member 133 and the midsole member 131 as discussed below. The layers can be formed of any flexible material, such as a flexible polymer material. In one embodiment, the layers 1366, 1368 are formed of a 0.05-0.2 mm thick pliable thin Mylar material. The insert 1337 is constructed by first depositing the conductive metallic material on the first layer 1366, such as by printing, in the traced pattern of the leads 1318, 1318A and the electrodes 1340, 1342 of the sensors 1316, to form the configuration shown in FIG. 27. Then, the additional carbon contact layer is deposited on the first layer 1366, tracing over the electrodes 1340, 1342 of the sensors 1316, and the carbon force-sensitive resistive material 1344 is deposited as puddles on the second layer 1368, as also shown in FIG. 27. After all the materials have been deposited, the layers 1366, 1368 are positioned in a superimposed manner, as shown in FIG. 28, so that the electrodes 1340, 1342 are aligned with the puddles of force-sensitive resistive material 1344, to form the insert member 1337 for insertion into the article of footwear 100. In one embodiment, the sensor system 1312 constructed in this manner can detect pressures in the range of 10-750 kPa with high sensitivity.

The sensor systems 212, 1312 shown in FIGS. 8 and 27-28 can be implemented within a shoe 100 between a foot-contacting member 133 and a midsole member 131 as shown in FIGS. 4 and 5. In one embodiment, the FSR sensor system 212, 1312 is inserted above the midsole member 131 (and above the strobel, if present) during manufacturing of the shoe 100 after connection of the upper 120 to the midsole 131 and outsole 132, and then the foot-contacting member 133 can be inserted over the sensor system 212, 1312. Additionally, in one embodiment, the sensor system 212, 1312 can be inserted as part of an insert member, such as the insert members 437 and 1337 shown in FIGS. 12 and 27-28. FIGS. 11-14 illustrate additional examples of implementing FSR sensors into an article of footwear, such as a shoe 100. The embodiments shown in FIGS. 11-14 illustrate the midsole member 131 having a well 135 therein for receiving an electronic module 22, and a port 14 for connection to the module 22, as described above and shown in FIG. 4. However, it is understood that the well 135 and/or the port 14 may be positioned elsewhere, such as wholly or partially within the foot contacting member 133, as shown in FIG. 5, or elsewhere in the shoe 100.

As one example, FIG. 11 illustrates a portion of a sole structure 130 for an article of footwear containing an FSR sensor system 312, with a midsole member 131 having an FSR sensor assembly 313 connected thereto. In this embodiment, the FSR sensors 316 are partially imbedded within the midsole member 131 and the sensor leads 318 are connected to the top surface of the midsole member 131. It is understood that the midsole member 131 may have a layer covering the sensors 316 to hold them within the midsole member 131, and that the sensors 318 may be wholly or partially imbedded within the midsole member 131, or the midsole member 131 may have "pockets" for insertion of the sensors 316. The midsole member 131 also has the port 14 connected thereto. The port 14 is connected to the sensor leads 318 and is positioned within the well 135 for connection with an electronic module 22 received within the well 135. The sensor leads 318 form an interface 319 proximate the port 14 for connection to the port 14.

As another example, FIG. 12 illustrates a portion of a sole structure 130 for an article of footwear containing an FSR sensor system 412, with an additional sole member 437 containing an FSR sensor assembly 413. In this embodiment, the additional sole member 437 is an insert or liner configured to be inserted between the foot contacting member 133 and the midsole member 131. The insert 437 has FSR sensors 416 and sensor leads 418 connected thereto. The insert 437 may have a configuration similar to the configuration of the insert 1337 described above and shown in FIGS. 27-28, or may have another configuration. Additionally, in this embodiment, the insert 437 is a thin layer of a flexible polymer webbing material having the FSR sensors 416 and the sensor leads 418 mounted thereon to hold the sensors in position. It is understood that the sensors 416 and/or the leads 418 may be wholly or partially embedded within the polymer material of the insert 437. In another embodiment, the insert 437 may consist entirely of the sensor assembly 413, without any binding or webbing material. The insert 437 is also configured for connection of the sensor leads 418 to the port 14 and is positioned such that when the insert 437 is positioned between the foot contacting 133 and the midsole 131, the interface(s) 419 of the sensor leads 418 will be within or adjacent to the well 135 for connection through the port 14 with an electronic module 22 received within the well 135. Additionally, the sole structure 130 can be provided with one or more other inserts 437 having sensors 416 in different configurations. These other inserts 437 can be removed and interchanged by lifting the foot contacting member 133 and replacing one insert with another, differently-configured insert 437. This allows a single article of footwear to be used with different sensor 416 configurations as desired, for different applications. For example, as described below, the sensor system 412 may be configured for communication with an external device 110, and different configurations of sensors 416 can be used for different games or other programs running on the external device 110. Further, the insert 437 may be sized so that it can be used in many different articles of footwear of different sizes, providing versatility.

In an alternate embodiment, shown in FIG. 13, an insert, liner, or other additional sole member 437A can be configured with a sensor assembly 412A for placement on top of an insole member 133. This insert 437A can be configured similarly to the insert 437 described above, such as having a flexible polymer webbing material that has sensors 416A and sensor leads 418A connected thereto. The sensor assembly 412A may contain extended and/or consolidated wire leads 418A that extend around or through the insole 133, terminating in an interface 419A configured to be connected to the port 14 positioned in the well 135 for connection to an electronic module 22. It is understood that this insert 437A may in some circumstances be considered a "foot contacting member," as the insert 437A forms a top part of the sole structure 130. Similarly to the insert 437 described above, the insert 437A can be removed and interchanged with other inserts 437A having different sensor 416A configurations, and may be sized for placement in footwear having various different sizes.

In another alternate embodiment, an insert member can be produced for connection to another sole member, such as a foot contacting member 133 or a midsole member 131. This insert member may be similar to the inserts 437 and 437A described above and shown in FIGS. 12-13, such as having a flexible webbing material (such as a polymer) that has sensors 416, 416A and sensor leads 418, 418A connected thereto. This configuration enables the sensor assembly 413, 413A to be mounted upon any member of the sole structure 130 as desired, to create a complete sensor system. The insert member may be connectable to a sole member in many different ways, such as by adhesives, fasteners, welding, heat-sealing, or any other suitable technique. It is understood that the insert member 437, 437A, in one embodiment, may have no webbing material and may include only the electronic components of the sensor assembly 413, 413A.

Figure 14:
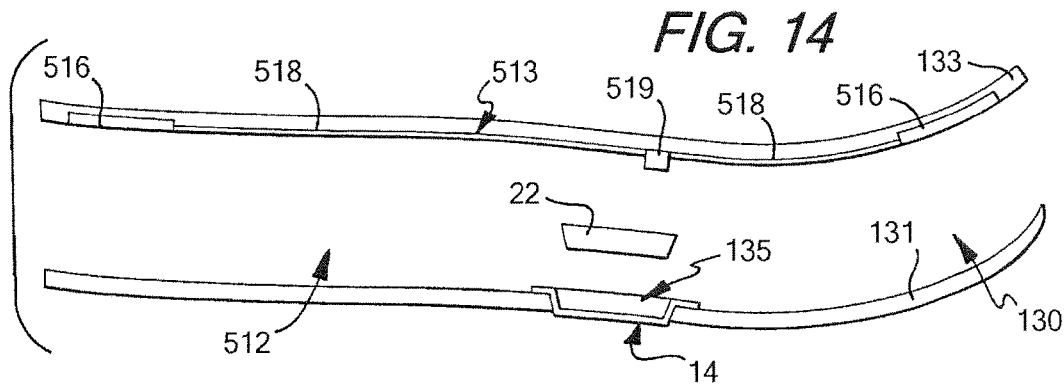

As a further example, FIG. 14 illustrates a portion of a sole structure 130 for an article of footwear containing an FSR sensor system 512, with a foot contacting member 133 having an FSR sensor assembly 513 connected thereto. The foot contacting member 133 illustrated in FIG. 14 is an insole member, however as described above, the foot contacting member 133 may alternately be a bootie element, a strobel, a sockliner, a sock, or other type of foot contacting member for use in an article of footwear. In this embodiment, the FSR sensors 516 are partially imbedded within the foot contacting member 133 and the sensor leads 518 are connected to the bottom surface of the foot contacting member 133. It is understood that the insole member 133 may have a layer covering the sensors 516 to hold them within the foot contacting member 133, and that the sensors 518 may be wholly or partially imbedded within the foot contacting member 133, or that the foot contacting member 133 may have pockets for receiving the sensors 516. The terminal ends of the sensor leads 518 are configured for connection to the port 14 and are positioned such that when the foot contacting member 133 is positioned on top of the midsole member 131, the interface 519 of the leads 518 will be within or adjacent to the well 135 for connection through the port 14 with an electronic module 22 received within the well 135. Additionally, the sole structure 130 can be provided with multiple foot contacting members 133 having sensor assemblies 513 in different configurations. These other foot contacting members 133 can be removed and interchanged by removing the foot contacting member 133 and replacing it with another foot contacting member 133 having sensors 516 in a different configuration. This allows a single article of footwear to be used with different sensor 516 configurations as desired, for different applications, including programs running on the external device 110, as described above.

Figure 15:
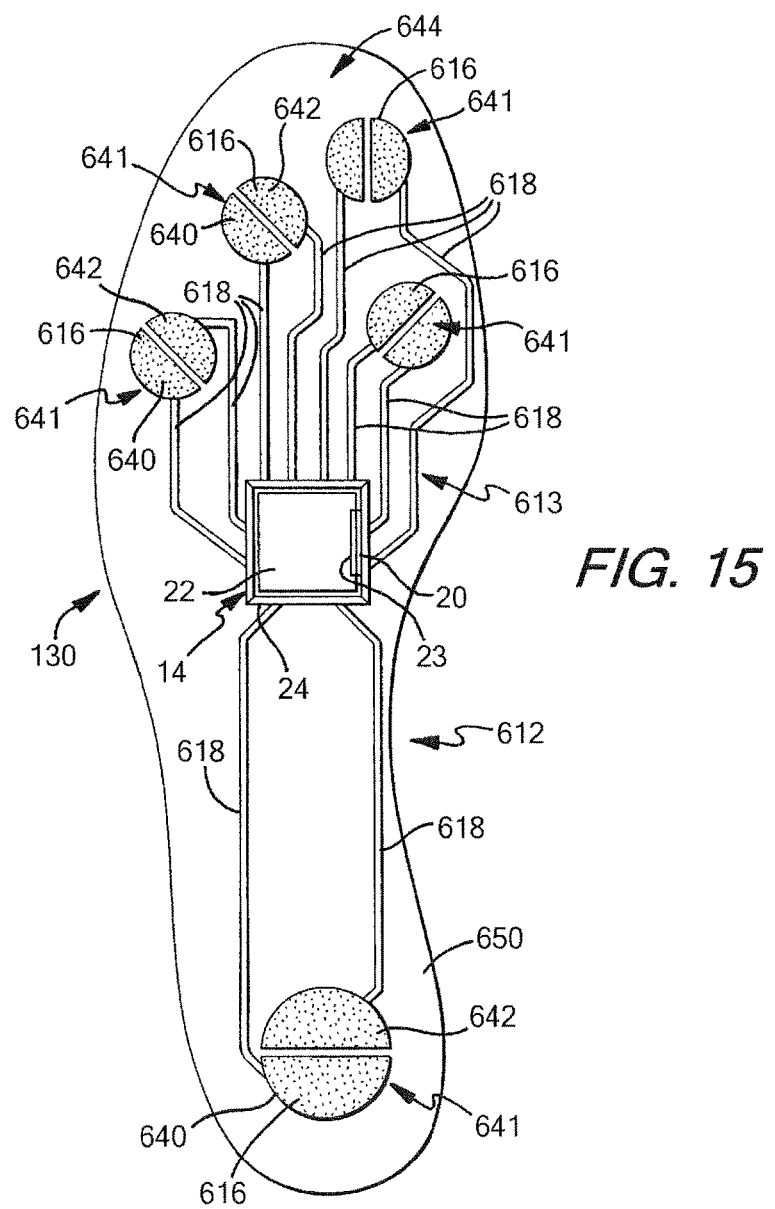
FIG. 15 is a top view of a sole of a shoe incorporating another embodiment of a sensor system utilizing separate electrodes and a force-sensitive resistive element.

FIG. 15 illustrates another exemplary embodiment of a shoe 100 that contains a sensor system 612 that includes a sensor assembly 613 incorporating a plurality of sensors 616. The sensors 616 utilize pairs 641 of electrodes 640, 642 and a separate force-sensitive resistive element 650, containing a force-sensitive resistive material 644 in contact with the electrodes 640, 642. In this embodiment, each electrode pair 641 and the force-sensitive material 644 combine to form a sensor 616 and operate similarly to the electrodes (+) and (−) and the material M described above and shown in FIGS. 9-10. The sensor system 612 can be arranged similarly to the sensor systems 12, 212 described above, and also includes a port 14 in communication with an electronic module 22 and a plurality of leads 618 connecting the electrodes 640, 642 to the port 14. The module 22 is contained within a well or cavity 135 in the sole structure 130 of the shoe 100, and the port 14 is connected within the well 135 to enable connection to the module 22 within the well 135.

The force-sensitive resistive element 650 in FIG. 15 can be any element that is positioned in contact with the electrodes 640, 642. The force-sensitive element 650 may be entirely composed of a force-sensitive resistive material 644, or may be only partially composed of the force-sensitive material 644, such as by including a layer of force-sensitive material 644 or strategically-placed areas containing the force-sensitive material 644. Additionally, the force-sensitive element 650 may be one continuous piece or may include several separate pieces. In one embodiment, such as the embodiments described below and shown in FIGS. 16-20, the force-sensitive element 650 may be contained in a member of the sole structure 130, or may entirely form a member of the sole structure 130.

One material that is suitable for use as the force-sensitive resistive material 244 is a quantum tunneling composite ("QTC"), which provides volume-based resistance behavior. A quantum tunneling composite generally includes a polymer matrix material that contains metallic particles or other conductive particles. Upon compression, the conductive particles move closer together, allowing electrons to tunnel quantum mechanically through the insulative polymer matrix. As the compression increases, the conductive particles move still closer together, allowing more electrical flow and decreasing the measured resistance. The particles in a quantum tunneling composite may have irregular surfaces, which can enable a greater relative range of movement of the particles without the particles contacting each other. This behavior allows for quantitative or binary (on/off) detection of force on the force-sensitive material. Suitable quantum tunneling composite materials can be obtained from Peratech Limited, among other sources.

Another material that is suitable for use as the force-sensitive resistive material 244 is a custom conductive foam, which also provides force-sensitive resistive behavior. A custom conductive foam generally includes a foam made from a conductive material or containing a conductive material additive, such as carbon black or other forms of carbon, or a conductive polymer. The custom conductive foam allows greater conduction of electrons as the foam is compressed, thus decreasing measured resistance. A further material that is suitable for use as the force-sensitive resistive material 244 is a force-transducing rubber. The force-sensitive material 644 may be any other material exhibiting force-sensitive resistive behavior, including any materials described above having volume-based or contact-based resistance.

The electrodes 640, 642 can be made from any of the materials described above with respect to electrodes 240, 242. In one embodiment, the electrodes 640, 642 and/or the leads 618 can be printed onto a surface, such as a foot contacting member 133, a midsole member 131, or another sole member, using a conductive ink. In another embodiment, conductive tape can be used for this purpose, as well as other structures and techniques described above.

The sensor system 612 shown in FIG. 15 can be implemented within a shoe 100 between a foot-contacting member 133 and a midsole member 131 as shown in FIGS. 4 and 5, such as by connecting the force-sensitive resistive element 650 to either the foot-contacting member 133 or the midsole member 131. FIGS. 11-20 illustrate additional examples of implementing sensors using a separate force-sensitive resistive element into an article of footwear, such as a shoe 100. The embodiments shown in FIGS. 11-20 illustrate the midsole member 131 having a well 135 therein for receiving an electronic module 22 and a port 14 for connection to the module 22, as described above and shown in FIG. 4. However, it is understood that the well 135 and/or the port 14 may be positioned elsewhere, such as wholly or partially within the foot contacting member 133, as shown in FIG. 5, or elsewhere in the shoe 100.

As one example, FIG. 16 illustrates a portion of a sole structure 130 for an article of footwear containing a sensor system 712, with a foot contacting member 133 having an electrode assembly 713 connected thereto. In this embodiment, the electrode assembly 713 includes electrode pairs 741 and sensor leads 718 that are connected to the bottom surface of the foot contacting member 133. In one embodiment, the electrode pairs 741 and the sensor leads 718 can be printed on the bottom of the foot contacting member 133, and in another embodiment, the electrode pairs 741 and leads 718 can be contained within a layer on the bottom of the foot contacting member 133. It is understood that the electrode pairs 741 and/or the leads 718 may be wholly or partially imbedded within the foot contacting member 133. The midsole member 131 contains a force-sensitive resistive element 750 in the form of a layer 751 of a force-sensitive resistive material 744 on the top surface thereof. It is understood that this layer 751 may not be continuous in some embodiments. The sensor leads 718 have an interface 719 positioned within or adjacent to the well 135 for connection through the port 14 with an electronic module 22 received within the well 135. Additionally, the sole structure 130 can be provided with multiple foot contacting members 133 having electrode assemblies 713 in different configurations. These other foot contacting members 133 can be removed and interchanged by removing the foot contacting member 133 and replacing it with another foot contacting member 133 having electrode pairs 741 in a different configuration. This allows a single article of footwear to be used with different sensor configurations as desired, for different applications, including programs running on the external device 110, as described above. It is also understood that this configuration can be reversed, with the foot contacting member 133 having the force-sensitive resistive element 750 connected thereto, and the electrode pairs 741 may be connected to the midsole member 131.

In another embodiment, shown in FIG. 17, the sole structure 130 contains a sensor system 812, with a foot contacting member 133 having an electrode assembly 813 connected thereto in the same configuration as the electrode assembly 713 described above and shown in FIG. 16. As similarly described above, the electrode assembly 813 includes electrode pairs 841 and sensor leads 818 that are connected to the bottom surface of the foot contacting member 133, with the leads 818 terminating in an interface 819 for connection to the port 14. However, in the embodiment of FIG. 17, the midsole member 131 itself functions as the force-sensitive resistive element 850, and is composed entirely of the force-sensitive resistive material 844. This embodiment otherwise functions in the same manner as the embodiment shown in FIG. 16, and provides the same interchangeability. It is also understood that this configuration can be reversed, with the foot contacting member 133 functioning as the force-sensitive resistive element 850, composed of the force-sensitive resistive material 844, and the electrode pairs 841 may be connected to the midsole member 131.

As another example, FIG. 18 illustrates a portion of a sole structure 130 for an article of footwear containing a sensor system 912, with a foot contacting member 133, a midsole member 131, and an additional sole member 937 having an electrode assembly 713 connected thereto, positioned between the midsole member 131 and the foot contacting member 133. The electrode assembly 913 includes electrode pairs 941 and sensor leads 918 that are connected to the additional sole member 937. In this embodiment, the additional sole member 133 is an insert 937 made from a thin layer of a flexible polymer webbing material having the electrode pairs 941 and the sensor leads 918 mounted thereon to hold the electrode pairs 941 in position. It is understood that the electrode pairs 941 and/or the leads 918 may be wholly or partially embedded within the polymer material of the insert 937. In another embodiment, the insert 937 may consist entirely of the electrode assembly 913, without any binding or webbing material. The midsole member 131 contains a force-sensitive resistive element 950 in the form of a layer 951 of a force-sensitive resistive material 944 on the top surface thereof, similarly to the force-sensitive resistive element 750 of FIG. 16. It is understood that this layer 951 may not be continuous in some embodiments. The insert 937 also is also configured for connection of the sensor leads 918 to the port 14 and is positioned such that when the insert 937 is positioned between the foot contacting 133 and the midsole 131, the interface 919 of the sensor leads 918 will be within or adjacent to the well 135 for connection through the port 14 with an electronic module 22 received within the well 135. Additionally, the sole structure 130 can be provided with multiple inserts 937 having electrode assemblies 913 in different configurations. These other inserts 937 can be removed and interchanged by lifting the foot contacting member 133 and replacing the insert 937 with another insert 937 having electrode pairs 941 in a different configuration. This allows a single article of footwear to be used with different sensor configurations as desired, for different applications, including programs running on the external device 110, as described above.

In another embodiment, shown in FIG. 19, the sole structure 130 contains a sensor system 1012, with an insert 1037 having an electrode assembly 1013 connected thereto in the same configuration as the electrode assembly 913 described above and shown in FIG. 18. As similarly described above, the electrode assembly 1013 includes electrode pairs 1041 and sensor leads 1018 that are connected to the insert 1037 positioned between the midsole member 131 and the foot contacting member 133, with the leads 1018 terminating in an interface 1019 for connection to the port 14. However, in the embodiment of FIG. 19, the midsole member 131 itself functions as the force-sensitive resistive element 1050, and is composed entirely of the force-sensitive resistive material 1044. This embodiment otherwise functions in the same manner as the embodiment shown in FIG. 18, and provides the same interchangeability. It is understood that, in an alternate embodiment, the foot contacting member 133 may be constructed of the force-sensitive resistive material 1044, functioning as the force-sensitive resistive element 1050. In this configuration, the insert 1037 and/or the electrode assembly 1013 may need to be reconfigured or repositioned to contact the force-sensitive material 1044 on the top side, rather than the bottom side of the insert 1037.

It is understood that, in an alternate embodiment, the inserts 937, 1037 shown in FIGS. 18-19 can be used with the insole member 133 containing or comprising the force-sensitive resistive element 950, 1050. Where the insole 133 has the layer 951 of the force-sensitive resistive material 944 located on the bottom surface thereof, rather than on the top surface of the midsole member 131, the insert 937 and/or the electrode assembly 913 may need to be reconfigured or re-oriented to contact the force-sensitive material 944 on the top side, rather than the bottom side of the insert 937. The insole 133 may also have the layer 951 of the force-sensitive material 944 on the top side thereof, in which case, the insert 937, 1037 can be inserted on the top side as well. It is understood that if the entire insole 133 comprises the force-sensitive resistive element 1050, the insert 937, 1037 can be used on either the top or bottom side of the insole 133.

In another embodiment, shown in FIG. 20, the sole structure 130 contains a sensor system 1112, with an insert 1137 having an electrode assembly 1113 connected thereto in the same configuration as the electrode assembly 913 described above and shown in FIG. 18. As similarly described above, the electrode assembly 1113 includes electrode pairs 1141 and sensor leads 1118 that are connected to the insert 1137 positioned between the midsole member 131 and the foot contacting member 133, with the leads 1118 terminating in an interface 1119 for connection to the port 14. However, in the embodiment of FIG. 20, the force-sensitive resistive element 1150 is contained in a separate liner 1151 of the force-sensitive resistive material 1144 that is not attached to the midsole member 131 or the foot contacting member 133. The liner 1151 may be entirely composed of the force-sensitive resistive material 1144, or may contain portions or areas composed of the force-sensitive material 1144. Additionally, in this embodiment, the liner 1151 is positioned between the midsole member 131 and the insert 1137, however in another embodiment, the liner 1151 may be positioned between the foot contacting member 133 and the insert 1137. It is understood that, if the position of the liner 1151 is changed, the insert 1137 and/or the electrode assembly 1113 may need to be reconfigured or repositioned to contact the force-sensitive material 1144 on the top side, rather than the bottom side of the insert 1137. Further, in other embodiments, the liner 1151 and insert 1137 can be positioned anywhere in the sole structure 130, as long as the electrode pairs 1141 are in contact with the force-sensitive material 1144. This embodiment otherwise functions in the same manner as the embodiment shown in FIG. 18, and provides the same interchangeability of different electrode assemblies. This embodiment also provides interchangeability of the force-sensitive element 1150, such as if a different material 1144 is desired or if the force-sensitive element becomes damaged or worn out.

In another alternate embodiment, an insert member can be produced for connection to another sole member, such as a foot contacting member 133 or a midsole member 131. This insert member may be similar to the inserts 937, 1037, 1137 described above and shown in FIGS. 18-20, such as having a flexible webbing material (such as a polymer) that has electrode pairs 941, 1041, 1141 and sensor leads 918, 1018, 1118 having ends configured for connection to the port 14, as described above. This configuration enables the electrode assembly 913, 1013, 1113 to be mounted upon any member of the sole structure 130 as desired, to create a complete sensor system. The insert member may be connectable to a sole member in many different ways, such as by adhesives, fasteners, welding, heat-sealing, or any other suitable technique. It is understood that the insert member 937, 1037, 1137, in one embodiment, may have no webbing material and may include only the electronic components of the sensor assembly 913, 1013, 1113.

It is understood that the quantum tunneling composites, custom conductive foams, force transducing rubbers, and other force-sensitive resistive materials discussed herein can be utilized to create individual, self-contained sensors, similar to the FSR sensors 216 described above and shown in FIG. 8, and are not limited to use in sensor assemblies having separate electrodes and force-sensitive elements. Such individual sensors may contain two electrodes and a force-sensitive resistive material, such as illustrated in FIGS. 9-10.

In an alternate embodiment, shown in FIG. 21, the sensor system 1212 may include a sensor assembly 1213 that is connected to the upper 120 of an article of footwear 100, rather than the sole structure 130. Any of the different types of sensors described above can be used in this embodiment, and the sensors can be connected to the upper 120 in any suitable manner. For example, in one embodiment, the sensors 1216 may be FSR sensors that are woven into the material of the upper, with conductive fabrics also woven into the upper to form the leads 1218. In this embodiment, the module 22 is shown contained in the sole 130 of the shoe 100, with the leads 1218 extending from the upper 120 underneath the foot-contacting member 133 to a port 14 in communication with the module 22. However, it is understood that the module 22 may be located elsewhere, including attached to the upper 120, in other embodiments.

The various interchangeable sole inserts described above herein can allow for custom development of sensor systems at a reasonable budget, including interchangeable inserts 437, 437A, 937, 1037, and 1137 having sensor/electrode assemblies 413, 413A, 913, 1013, and 1113, as well as interchangeable foot contacting members 133 having sensor/electrode assemblies 513, 713, and 813. For example, FSR sensor inserts 437 and 437A and the foot contacting member 133 having FSR sensor assembly 513 can be custom-manufactured for various purposes by various different sources, and can be inserted in a wide variety of footwear 100. As another example, inserts 937, 1037, and 1137 and foot contacting members 133 having electrode assemblies 713, 813, 913, 1013, and 1113 can similarly be custom-manufactured and inserted in a wide variety of footwear 100. In one embodiment, footwear 100 can be manufactured containing a force-sensitive resistive material, and any of the sensor assembly configurations 713, 813, 913, 1013, and 1113 can be inserted into the footwear 100 to function with the force-sensitive material. As described above, separate liners 1151 of the force-sensitive resistive material 1144 can also be manufactured for insertion into a wide variety of footwear, further increasing the versatility of the system. As described below, such sensor assemblies can be customized for use with specific software for the electronic module 22 and/or the external device 110. A third party may provide such software along with a sole insert having a customized sensor assembly, as a package.

The operation and use of the sensor systems 12, 212, 312, 412, 412A, 512, 612, 712, 812, 912, 1012, 1112, 1212 are described below with respect to the sensor system 12 shown in FIGS. 3-5, and it is understood that the principles of operation of the sensor system 12, including all embodiments and variations thereof, are applicable to the other embodiments of the sensor systems 212, 312, 412, 412A, 512, 612, 712, 812, 912, 1012, 1112, 1212 described above. In operation, the sensors 16 gather data according to their function and design, and transmit the data to the port 14. The port 14 then allows the electronic module 22 to interface with the sensors 16 and collect the data for later use and/or processing. In one embodiment, the data is collected, stored, and transmitted in a universally readable format, so the data is able to be accessed and/or downloaded by a plurality of users, with a variety of different applications, for use in a variety of different purposes. In one example, the data is collected, stored, and transmitted in XML format.

In different embodiments, the sensor system 12 may be configured to collect different types of data. In one embodiment (described above), the sensor(s) 16 can collect data regarding the number, sequence, and/or frequency of compressions. For example, the system 12 can record the number or frequency of steps, jumps, cuts, kicks, or other compressive forces incurred while wearing the footwear 100, as well as other parameters, such as contact time and flight time. Both quantitative sensors and binary on/off type sensors can gather this data. In another example, the system can record the sequence of compressive forces incurred by the footwear, which can be used for purposes such as determining foot pronation or supination, weight transfer, foot strike patterns, or other such applications. In another embodiment (also described above), the sensor(s) 16 are able to quantitatively measure the compressive forces on the adjacent portions of the shoe 100, and the data consequently can include quantitative compressive force and/or impact measurement. Relative differences in the forces on different portions of the shoe 100 can be utilized in determining weight distribution and "center of pressure" of the shoe 100. The weight distribution and/or center of pressure can be calculated independently for one or both shoes 100, or can be calculated over both shoes together, such as to find a center of pressure or center of weight distribution for a person's entire body. As described above, a relatively densely packed array of on/off binary sensors can be used to measure quantitative forces by changes detected in "puddling" activation of the sensors during moments of greater compression. In further embodiments, the sensor(s) 16 may be able to measure rates of changes in compressive force, contact time, flight time or time between impacts (such as for jumping or running), and/or other temporally-dependent parameters. It is understood that, in any embodiment, the sensors 16 may require a certain threshold force or impact before registering the force/impact.

As described above, the data is provided through the universal port 14 to the module 22 in a universally readable format, so that the number of applications, users, and programs that can use the data is nearly unlimited. Thus, the port 14 and module 22 are configured and/or programmed as desired by a user, and the port 14 and module 22 receive input data from the sensor system 12, which data can be used in any manner desired for different applications. In many applications, the data is further processed by the module 22 and/or the external device 110 prior to use. In configurations where the external device 110 further processes the data, the module 22 may transmit the data to the external device 110. This transmitted data may be transmitted in the same universally-readable format, or may be transmitted in another format, and the module 22 may be configured to change the format of the data. Additionally, the module 22 can be configured and/or programmed to gather, utilize, and/or process data from the sensors 16 for one or more specific applications. In one embodiment, the module 22 is configured for gathering, utilizing, and/or processing data for use in a plurality of applications. Examples of such uses and applications are given below. As used herein, the term "application" refers generally to a particular use, and does not necessarily refer to use in a computer program application, as that term is used in the computer arts. Nevertheless, a particular application may be embodied wholly or partially in a computer program application.

Further, as illustrated in the embodiment of FIG. 22, the module 22 can be removed from the footwear 100 and replaced with a second module 22A configured for operating differently than the first module 22. In the embodiment of FIG. 22, the replacement is accomplished by lifting the insole member 133, disconnecting the first module 22 from the port 14 and removing the first module 22 from the well 135, then inserting the second module 22A into the well 135 and connecting the second module 22A to the port 14, and finally placing the insole member 133 back into position. The second module 22A may be programmed and/or configured differently than the first module 22. In one embodiment, the first module 22 may be configured for use in one or more specific applications, and the second module 22A may be configured for use in one or more different applications. For example, the first module 22 may be configured for use in one or more gaming applications and the second module 22A may be configured for use in one or more athletic performance monitoring applications. Additionally, the modules 22, 22A may be configured for use in different applications of the same type. For example, the first module 22 may be configured for use in one game or athletic performance monitoring application, and the second module 22A may be configured for use in a different game or athletic performance monitoring application. As another example, the modules 22, 22A may be configured for different uses within the same game or performance monitoring application. In another embodiment, the first module 22 may be configured to gather one type of data, and the second module 22A may be configured to gather a different type of data. Examples of such types of data are described herein, including quantitative force measurement, relative force measurement (i.e. sensors 16 relative to each other), weight shifting/transfer, impact sequences (such as for foot strike patterns) rate of force change, etc. In a further embodiment, the first module 22 may be configured to utilize or process data from the sensors 16 in a different manner than the second module 22A. For example, the modules 22, 22A may be configured to only gather, store, and/or communicate data, or the modules 22, 22A may be configured to further process the data in some manner, such as organizing the data, changing the form of the data, performing calculations using the data, etc. In yet another embodiment, the modules 22, 22A may be configured to communicate differently, such as having different communication interfaces or being configured to communicate with different external devices 110. The modules 22, 22A may function differently in other aspects as well, including both structural and functional aspects, such as using different power sources or including additional or different hardware components, such as additional sensors as described above (e.g. GPS, accelerometer, etc.).

One use contemplated for the data collected by the system 12 is in measuring weight transfer, which is important for many athletic activities, such as a golf swing, a baseball/softball swing, a hockey swing (ice hockey or field hockey), a tennis swing, throwing/pitching a ball, etc. The pressure data collected by the system 12 can give valuable feedback regarding balance and stability for use in improving technique in any applicable athletic field. It is understood that more or less expensive and complex sensor systems 12 may be designed, based on the intended use of the data collected thereby.

The data collected by the system 12 can be used in measurement of a variety of other athletic performance characteristics. The data can be used to measure the degree and/or speed of foot pronation/supination, foot strike patterns, balance, and other such parameters, which can be used to improve technique in running/jogging or other athletic activities. With regard to pronation/supination, analysis of the data can also be used as a predictor of pronation/supination. Speed and distance monitoring can be performed, which may include pedometer-based measurements, such as contact measurement or loft time measurement. Jump height can also be measured, such as by using contact or loft time measurement. Lateral cutting force can be measured, including differential forces applied to different parts of the shoe 100 during cutting. The sensors 16 can also be positioned to measure shearing forces, such as a foot slipping laterally within the shoe 100. As one example, additional sensors may be incorporated into the sides of the upper 120 of the shoe 100 to sense forces against the sides. As another example, a high-density array of binary sensors could detect shearing action through lateral changes in "puddling" of the activated sensors.

In another embodiment, described above, one or more sensors 1216 can additionally or alternately be incorporated into the upper 120 of the shoe 100. The sensors 1216 can be incorporated into the upper 120 in any manner described above. For example, the sensors 1216 may be woven into the material of the upper, with conductive fabrics also woven into the upper to form leads. In this configuration, additional parameters can be measured, such as kick force, such as for soccer or football, as well as number and/or frequency of "touches" in soccer.

The data, or the measurements derived therefrom, may be useful for athletic training purposes, including improving speed, power, quickness, consistency, technique, etc. The port 14, module 22, and/or external device 110 can be configured to give the user active, real-time feedback. In one example, the port 14 and/or module 22 can be placed in communication with a computer, mobile device, etc., in order to convey results in real time. In another example, one or more vibration elements may be included in the shoe 100, which can give a user feedback by vibrating a portion of the shoe to help control motion, such as the features disclosed in U.S. Pat. No. 6,978,684, which is incorporated herein by reference and made part hereof. Additionally, the data can be used to compare athletic movements, such as comparing a movement with a user's past movements to show consistency, improvement, or the lack thereof, or comparing a user's movement with the same movement of another, such as a professional golfer's swing. Further, the system 12 may be used to record biomechanical data for a "signature" athletic movement of an athlete. This data could be provided to others for use in duplicating or simulating the movement, such as for use in gaming applications or in a shadow application that overlays a movement over a user's similar movement.

The system 12 can also be configured for "all day activity" tracking, to record the various activities a user engages in over the course of a day. The system 12 may include a special algorithm for this purpose, such as in the module 22, the external device 110, and/or the sensors 16.

The system 12 may also be used for control applications, rather than data collection and processing applications. In other words, the system 12 could be incorporated into footwear, or another article that encounters bodily contact, for use in controlling an external device 110, such as a computer, television, video game, etc., based on movements by the user detected by the sensors 16. In effect, the footwear with the incorporated sensors 16 and leads 18 extending to a universal port 14 allows the footwear to act as an input system, and the electronic module 22 can be configured, programmed, and adapted to accept the input from the sensors 16 and use this input data in any desired manner, e.g., as a control input for a remote system. For example, a shoe with sensor controls could be used as a control or input device for a computer, or for a program being executed by the computer, similarly to a mouse, where certain foot movements, gestures, etc. (e.g., a foot tap, double foot tap, heel tap, double heel tap, side-to-side foot movement, footpoint, foot-flex, etc.) can control a pre-designated operation on a computer (e.g., page down, page up, undo, copy, cut, paste, save, close, etc.). Software can be provided to assign foot gestures to different computer function controls for this purpose. It is contemplated that an operating system could be configured to receive and recognize control input from the sensor system 12. Televisions or other external electronic devices can be controlled in this manner. Footwear 100 incorporating the system 12 can also be used in gaming applications and game programs, similarly to the Nintendo Wii controller, where specific movements can be assigned certain functions and/or can be used to produce a virtual representation of the user's motion on a display screen. As one example, center of pressure data and other weight distribution data can be used in gaming applications, which may involve virtual representations of balancing, weight shifting, and other performance activities. The system 12 can be used as an exclusive controller for a game or other computer system, or as a complementary controller. Examples of configurations and methods of using sensor systems for articles of footwear as controls for external devices and foot gestures for such controls are shown and described in U.S. Provisional Application No. 61/138,048, which is incorporated by reference herein in its entirety.

Figure 23:
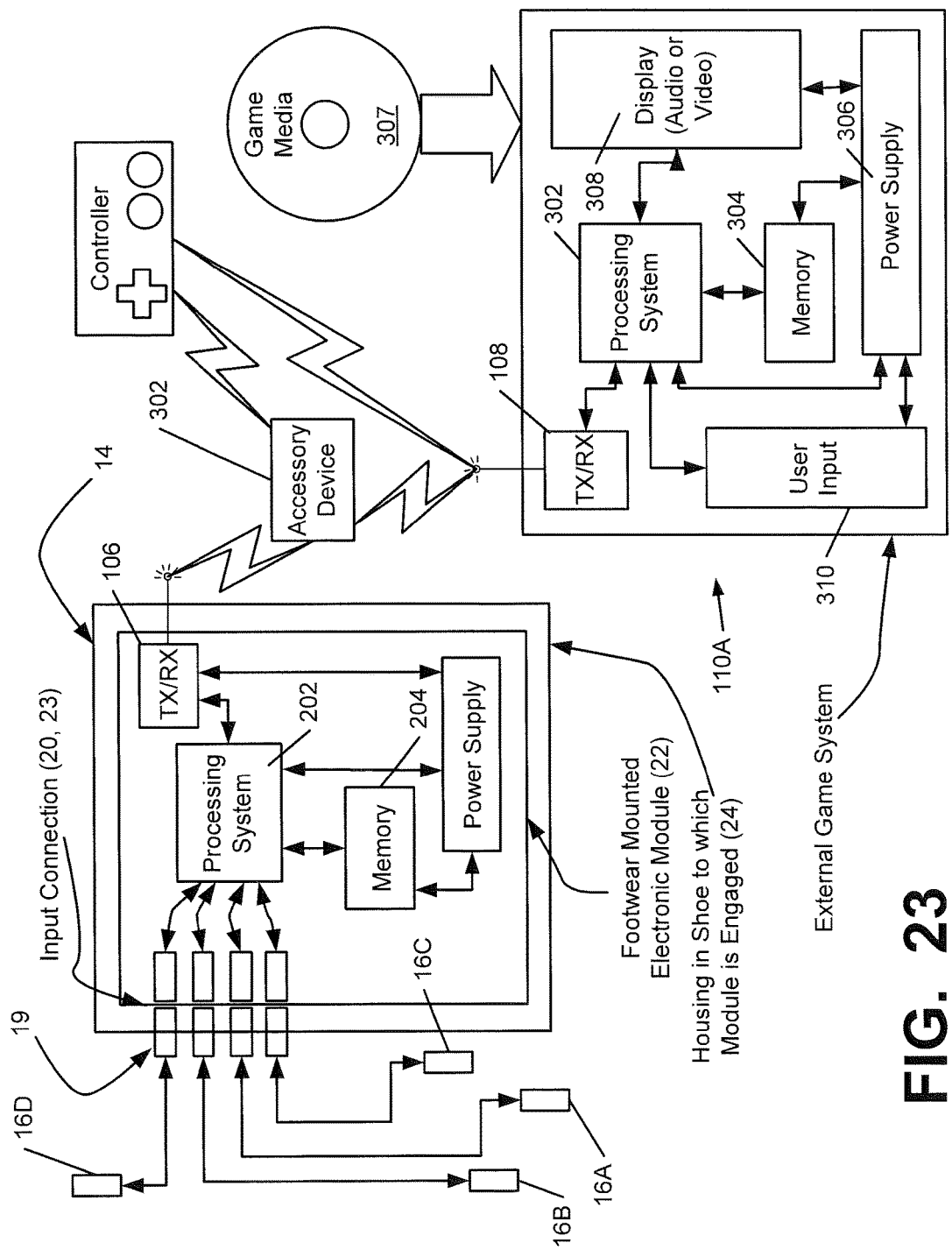
FIG. 23 is a schematic diagram of the electronic module of FIG. 6, in communication with an external gaming device.

Additionally, the system 12 may be configured to communicate directly with the external device 110 and/or with a controller for the external device. As described above, FIG. 6 illustrates one embodiment for communication between the electronic module 22 and the external device. In another embodiment, shown in FIG. 23, the system 12 can be configured for communication with an external gaming device 110A. The external gaming device 110A contains similar components to the exemplary external device 110 shown in FIG. 6. The external gaming device 110A also includes at least one game media 307 containing a game program (e.g. a cartridge, CD, DVD, Blu-Ray, or other storage device), and at least one remote controller 305 configured to communicate by wired and/or wireless connection through the transmitting/receiving element 108. In the embodiment shown, the controller 305 complements the user input 310, however in one embodiment, the controller 305 may function as the sole user input. In this embodiment, the system 12 is provided with an accessory device 303, such as a wireless transmitter/receiver with a USB plug-in, that is configured to be connected to the external device 110 and/or the controller 305 to enable communication with the module 22. In one embodiment, the accessory device 303 may be configured to be connected to one or more additional controllers and/or external devices, of the same and/or different type than the controller 305 and the external device 110. It is understood that if the system 12 includes other types of sensors described above (e.g., an accelerometer), such additional sensors can also be incorporated into controlling a game or other program on an external device 110.

An external device 110, such as a computer/gaming system, can be provided with other types of software to interact with the system 12. For example, a gaming program may be configured to alter the attributes of an in-game character based on a user's real-life activities, which can encourage exercise or greater activity by the user. In another example, a program may be configured to display an avatar of the user that acts in relation or proportion to the user activity collected by the sensing system of the shoe. In such a configuration, the avatar may appear excited, energetic, etc., if the user has been active, and the avatar may appear sleepy, lazy, etc., if the user has been inactive. The sensor system 12 could also be configured for more elaborate sensing to record data describing a "signature move" of an athlete, which could then be utilized for various purposes, such as in a gaming system or modeling system.

Figure 24:
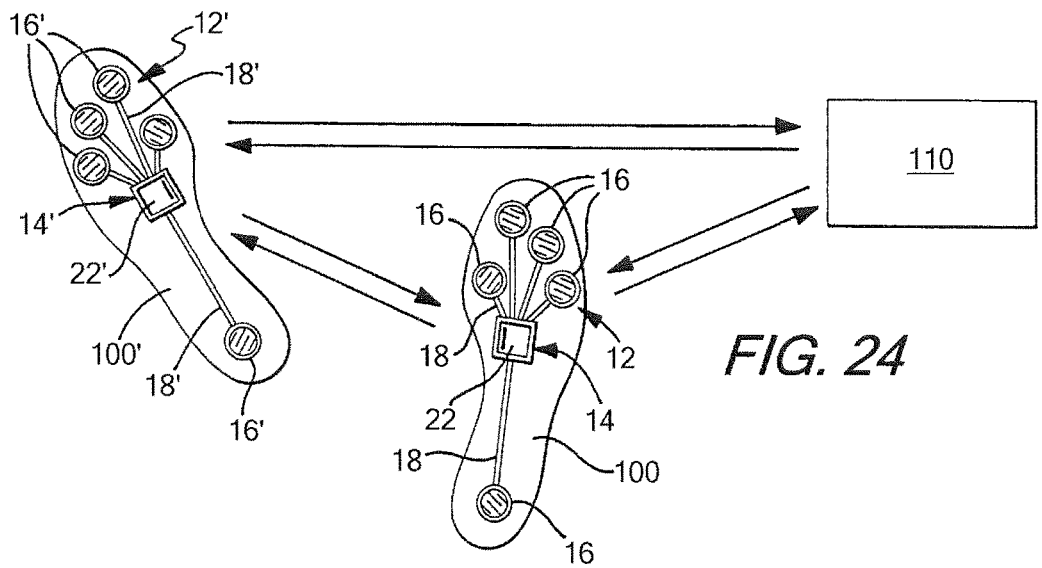
FIG. 24 is a schematic diagram of a pair of shoes, each containing a sensor system, in a mesh communication mode with an external device.
Figure 25:
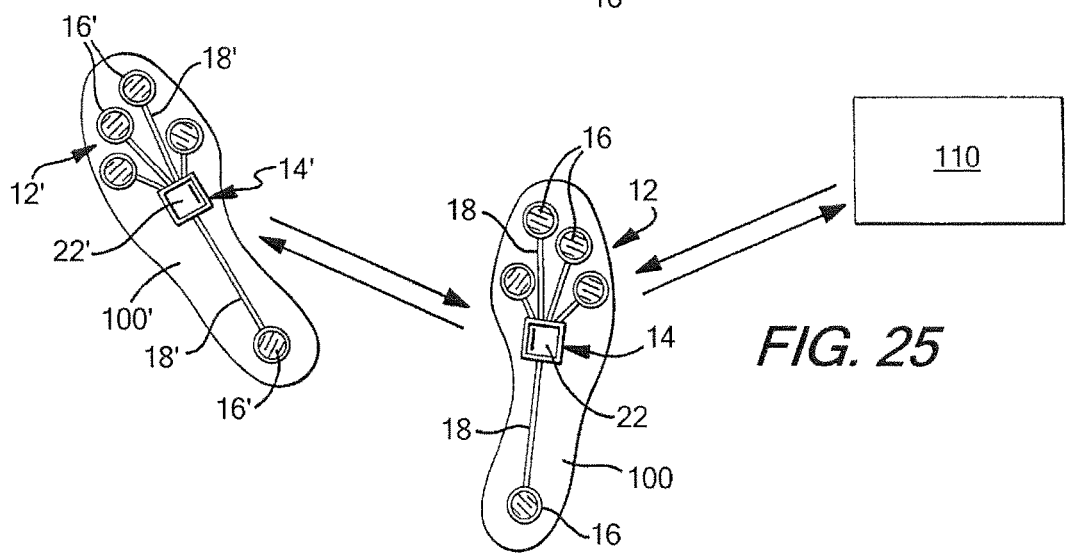
FIG. 25 is a schematic diagram of a pair of shoes, each containing a sensor system, in a "daisy chain" communication mode with an external device.
Figure 26:
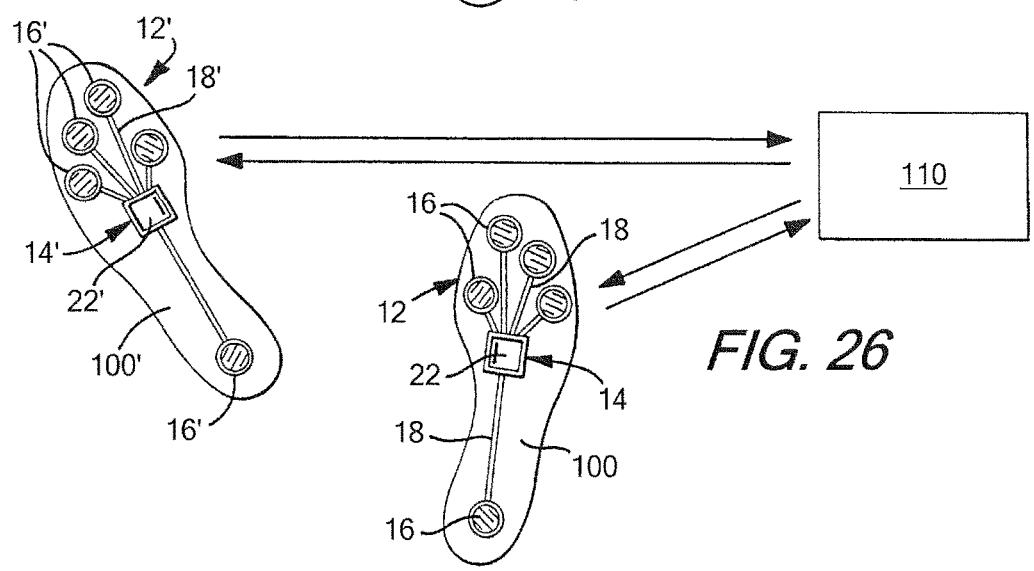
FIG. 26 is a schematic diagram of a pair of shoes, each containing a sensor system, in an independent communication mode with an external device.

A single article of footwear 100 containing the sensor system 12 as described herein can be used alone or in combination with a second article of footwear 100' having its own sensor system 12', such as a pair of shoes 100, 100' as illustrated in FIGS. 24-26. The sensor system 12' of the second shoe 100' generally contains one or more sensors 16' connected by sensor leads 18' to a port 14' in communication with an electronic module 22'. The second sensor system 12' of the second shoe 100' shown in FIGS. 24-26 has the same configuration as the sensor system 12 of the first shoe 100. However, in another embodiment, the shoes 100, 100' may have sensor systems 12, 12' having different configurations. The two shoes 100, 100' are both configured for communication with the external device 110, and in the embodiment illustrated, each of the shoes 100, 100' has an electronic module 22, 22' configured for communication with the external device 110. In another embodiment, both shoes 100, 100' may have ports 14, 14' configured for communication with the same electronic module 22. In this embodiment, at least one shoe 100, 100' may be configured for wireless communication with the module 22. FIGS. 24-26 illustrate various modes for communication between the modules 22, 22'

FIG. 24 illustrates a "mesh" communication mode, where the modules 22, 22' are configured for communicating with each other, and are also configured for independent communication with the external device 110. FIG. 25 illustrates a "daisy chain" communication mode, where one module 22' communicates with the external device 110 through the other module 22. In other words, the second module 22' is configured to communicate signals (which may include data) to the first module 22, and the first module 22 is configured to communicate signals from both modules 22, 22' to the external device 110. Likewise, the external device communicates with the second module 22' through the first module 22, by sending signals to the first module 22, which communicates the signals to the second module 22'. In one embodiment, the modules 22, 22' can also communicate with each other for purposes other than transmitting signals to and from the external device 110. FIG. 26 illustrates an "independent" communication mode, where each module 22, 22' is configured for independent communication with the external device 110, and the modules 22, 22' are not configured for communication with each other. In other embodiments, the sensor systems 12, 12' may be configured for communication with each other and/or with the external device 110 in another manner.

Still other uses and applications of the data collected by the system 12 are contemplated within the scope of the invention and are recognizable to those skilled in the art.

As will be appreciated by one of skill in the art upon reading the present disclosure, various aspects described herein may be embodied as a method, a data processing system, or a computer program product. Accordingly, those aspects may take the form of an entirely hardware embodiment, an entirely software embodiment or an embodiment combining software and hardware aspects. Furthermore, such aspects may take the form of a computer program product stored by one or more tangible computer-readable storage media or storage devices having computer-readable program code, or instructions, embodied in or on the storage media. Any suitable tangible computer readable storage media may be utilized, including hard disks, CD-ROMs, optical storage devices, magnetic storage devices, and/or any combination thereof. In addition, various intangible signals representing data or events as described herein may be transferred between a source and a destination in the form of electromagnetic waves traveling through signal-conducting media such as metal wires, optical fibers, and/or wireless transmission media (e.g., air and/or space).

As described above, aspects of the present invention may be described in the general context of computer-executable instructions, such as program modules, being executed by a computer and/or a processor thereof. Generally, program modules include routines, programs, objects, components, data structures, etc. that perform particular tasks or implement particular abstract data types. Such a program module may be contained in a tangible computer-readable medium, as described above. Aspects of the present invention may also be practiced in distributed computing environments where tasks are performed by remote processing devices that are linked through a communications network. Program modules may be located in a memory, such as the memory 204 of the module 22 or memory 304 of the external device 110, or an external medium, such as game media 307, which may include both local and remote computer storage media including memory storage devices. It is understood that the module 22, the external device 110, and/or external media may include complementary program modules for use together, such as in a particular application. It is also understood that a single processor 202, 302 and single memory 204, 304 are shown and described in the module 22 and the external device 110 for sake of simplicity, and that the processor 202, 302 and memory 204, 304 may include a plurality of processors and/or memories respectively, and may comprise a system of processors and/or memories.

The various embodiments of the sensor system described herein, as well as the articles of footwear, foot contacting members, inserts, and other structures incorporating the sensor system, provide benefits and advantages over existing technology. For example, many of the sensor embodiments described herein provide relatively low cost and durable options for sensor systems, so that a sensor system can be incorporated into articles of footwear with little added cost and good reliability. As a result, footwear can be manufactured with integral sensor systems regardless of whether the sensor systems are ultimately desired to be used by the consumer, without appreciably affecting price. Additionally, sole inserts with customized sensor systems can be inexpensively manufactured and distributed along with software designed to utilize the sensor systems, without appreciably affecting the cost of the software. As another example, the sensor system provides a wide range of functionality for a wide variety of applications, including gaming, fitness, athletic training and improvement, practical controls for computers and other devices, and many others described herein and recognizable to those skilled in the art. In one embodiment, third-party software developers can develop software configured to run using input from the sensor systems, including games and other programs. The ability of the sensor system to provide data in a universally readable format greatly expands the range of third party software and other applications for which the sensor system can be used. As a further example, the various sole inserts containing sensor systems, including liners, insoles, and other elements, permit interchangeability and customization of the sensor system for different applications.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed is:

1. A system comprising:
   a first electronic module configured for communication with an external device;
   a first article of footwear comprising a first upper member and a first sole structure engaged with the first upper member, wherein the first upper member and the first sole structure combine to at least partially define a first foot-receiving chamber, the first sole structure including a first foot contacting member partially defining the first foot receiving chamber;
   a first insert engaged with the first sole structure and positioned below the first foot contacting member, the first insert comprising:
      a first insert member at least partially formed of a foam material;
      a plurality of first force sensors connected to the first insert member and configured to sense a force exerted on the first insert by a foot of a user, wherein the first force sensors include a first phalange sensor, a first metatarsal sensor, a fifth metatarsal sensor, and a heel sensor;
      a first port configured for removable connection to the first electronic module; and
      a plurality of first leads connected to the first insert member, the first leads extending from the first force sensors to the first port, such that the first port is configured to enable communication between the first force sensors and the first electronic module through the first leads when the first electronic module is connected to the first port;
   a second electronic module configured for communication with the external device;
   a second article of footwear comprising a second upper member and a second sole structure engaged with the second upper member, wherein the second upper member and the second sole structure combine to at least partially define a second foot-receiving chamber, the second sole structure including a second foot contacting member partially defining the second foot receiving chamber; and
   a second insert engaged with the second sole structure and positioned below the second foot contacting member, the second insert comprising:
      a second insert member at least partially formed of a foam material;
      a plurality of second force sensors connected to the second insert member and configured to sense a force exerted on the second insert by a foot of a user, wherein the second force sensors include a first phalange sensor, a first metatarsal sensor, a fifth metatarsal sensor, and a heel sensor;
      a second port configured for removable connection to the second electronic module; and
      a plurality of second leads connected to the second insert member, the second leads extending from the second force sensors to the second port, such that the second port is configured to enable communication between the second force sensors and the second electronic module through the second leads when the second electronic module is connected to the second port,
   wherein the first electronic module is configured to collect first force data from the first force sensors, and the second electronic module is configured to collect second force data from the second force sensors, and wherein the first and second electronic modules are further configured to transmit the first and second force data to the external device to enable further processing of the first and second force data by the external device.

2. The system of claim 1, further comprising the external device, wherein the external device comprises a memory and a processor, wherein the external device is configured for receiving the first and second force data, storing the first and second force data in the memory, and further processing the first and second force data.

3. The system of claim 2, wherein the first and second electronic modules are configured for transmitting the first and second force data to the external device in real time, and wherein the external device further comprises a display and is configured for displaying feedback to the user based on the first and second force data in real time.

4. The system of claim 1, wherein the first port is located outside of the first insert member, and the second port is located outside of the second insert member.

5. The system of claim 4, wherein the first port is located within the first sole structure beneath the first foot contacting member, and the second port is located within the second sole structure beneath the second foot contacting member.

6. The system of claim 1, wherein the first and second leads comprise wire leads.

7. The system of claim 1, wherein the first leads have terminal ends that converge to a first location to form a first consolidated interface, wherein the first consolidated interface is located at the first port, such that the first port is configured to enable communication between the first force sensors and the first electronic module through the first leads and the first consolidated interface when the first electronic module is connected to the first port, and wherein the second leads have terminal ends that converge to a second location to form a second consolidated interface, wherein the second consolidated interface is located at the second port, such that the second port is configured to enable communication between the second force sensors and the second electronic module through the second leads and the second consolidated interface when the second electronic module is connected to the second port.

8. The system of claim 1, wherein the first leads further comprise a first power lead extending from the first port and connected to all of the first force sensors, and wherein the first power lead is configured for providing electrical power from the first electronic module to all of the first force sensors when the first electronic module is connected to the first port, and wherein the second leads further comprise a second power lead extending from the second port and connected to all of the second force sensors, and wherein the second power lead is configured for providing electrical power from the second electronic module to all of the second force sensors when the second electronic module is connected to the second port.

9. A system comprising:
   a first insert configured to be engaged with a first sole structure of a first article of footwear, the first insert comprising:
      a first insert member at least partially formed of a foam material;
      a plurality of first force sensors connected to the first insert member and configured to sense a force exerted on the first insert by a foot of a user, wherein the first force sensors include a first phalange sensor, a first metatarsal sensor, a fifth metatarsal sensor, and a heel sensor;
      a plurality of first leads connected to the first insert member, the first leads extending from the first force sensors and having terminal ends that converge to a first location to form a first consolidated interface; and
      a first port configured for removable connection to a first electronic module, wherein the first consolidated interface is located at the first port, such that the first port is configured to enable communication between the first force sensors and the first electronic module through the first leads and the first consolidated interface when the first electronic module is connected to the first port; and
   a second insert configured to be engaged with a second sole structure of a second article of footwear, the second insert comprising:
      a second insert member at least partially formed of a foam material;
      a plurality of second force sensors connected to the second insert member and configured to sense a force exerted on the second insert by a foot of a user, wherein the second force sensors include a first phalange sensor, a first metatarsal sensor, a fifth metatarsal sensor, and a heel sensor;
      a plurality of second leads connected to the second insert member, the second leads extending from the second force sensors and having terminal ends that converge to a second location to form a second consolidated interface; and
      a second port configured for removable connection to a second electronic module, wherein the second consolidated interface is located at the second port, such that the second port is configured to enable communication between the second force sensors and the second electronic module through the second leads and the second consolidated interface when the second electronic module is connected to the second port.

10. The system of claim 9, wherein the first port is located outside of the first insert member, and the second port is located outside of the second insert member.

11. The system of claim 10, wherein the first port is located below the first insert member, and the second port is located below the second insert member.

12. The system of claim 9, wherein the first and second leads comprise wire leads.

13. The system of claim 9, wherein the first leads further comprise a first power lead extending from the first port and connected to all of the first force sensors, and wherein the first power lead is configured for providing electrical power from the first electronic module to all of the first force sensors when the first electronic module is connected to the first port, and wherein the second leads further comprise a second power lead extending from the second port and connected to all of the second force sensors, and wherein the second power lead is configured for providing electrical power from the second electronic module to all of the second force sensors when the second electronic module is connected to the second port.

14. The system of claim 9, further comprising the first electronic module and the second electronic module, wherein the first electronic module is configured to collect first force data from the first force sensors, and the second electronic module is configured to collect second force data from the second force sensors, and wherein the first and second electronic modules are configured for communication with an external device, and the first and second electronic modules are further configured to transmit the first and second force data to the external device to enable further processing of the first and second force data by the external device.

15. The system of claim 14, wherein the first and second electronic modules are configured for transmitting the first and second force data to the external device in real time.

16. A system comprising:
   a first insert configured to be engaged with a first sole structure of a first article of footwear, the first insert comprising:
      a first insert member at least partially formed of a foam material;

a plurality of first force sensors connected to the first insert member and configured to sense a force exerted on the first insert by a foot of a user, wherein the first force sensors include a first phalange sensor, a first metatarsal sensor, a fifth metatarsal sensor, and a heel sensor;

a first port configured for removable connection to a first electronic module; and a plurality of first leads connected to the first insert member, the first leads extending from the first force sensors to the first port, such that the first port is configured to enable communication between the first force sensors and the first electronic module through the first leads when the first electronic module is connected to the first port, wherein the first leads further comprise a first power lead extending from the first port and connected to all of the first force sensors, and wherein the first power lead is configured for providing electrical power from the first electronic module to all of the first force sensors when the first electronic module is connected to the first port;

a second insert configured to be engaged with a second sole structure of a second article of footwear, the second insert comprising:

a second insert member at least partially formed of a foam material;

a plurality of second force sensors connected to the second insert member and configured to sense a force exerted on the second insert by a foot of a user, wherein the second force sensors include a first phalange sensor, a first metatarsal sensor, a fifth metatarsal sensor, and a heel sensor;

a second port configured for removable connection to a second electronic module; and a plurality of second leads connected to the second insert member, the second leads extending from the second force sensors to the second port, such that the second port is configured to enable communication between the second force sensors and the second electronic module through the second leads when the second electronic module is connected to the second port, wherein the second leads further comprise a second power lead extending from the second port and connected to all of the second force sensors, and wherein the second power lead is configured for providing electrical power from the second electronic module to all of the second force sensors when the second electronic module is connected to the second port.

17. The system of claim 16, wherein the first port is located outside of the first insert member, and the second port is located outside of the second insert member.

18. The system of claim 17, wherein the first port is located below the first insert member, and the second port is located below the second insert member.

19. The system of claim 16, wherein the first and second leads comprise wire leads.

20. The system of claim 16, wherein the first leads have terminal ends that converge to a first location to form a first consolidated interface, wherein the first consolidated interface is located at the first port, such that the first port is configured to enable communication between the first force sensors and the first electronic module through the first leads and the first consolidated interface when the first electronic module is connected to the first port, and wherein the second leads have terminal ends that converge to a second location to form a second consolidated interface, wherein the second consolidated interface is located at the second port, such that the second port is configured to enable communication between the second force sensors and the second electronic module through the second leads and the second consolidated interface when the second electronic module is connected to the second port.

21. The system of claim 16, further comprising the first electronic module and the second electronic module, wherein the first electronic module is configured to collect first force data from the first force sensors, and the second electronic module is configured to collect second force data from the second force sensors, and wherein the first and second electronic modules are configured for communication with an external device, and the first and second electronic modules are further configured to transmit the first and second force data to the external device to enable further processing of the first and second force data by the external device.

22. The system of claim 21, wherein the first and second electronic modules are configured for transmitting the first and second force data to the external device in real time.

* * * * *